(12) United States Patent
Sandstedt et al.

(10) Patent No.: US 10,010,406 B2
(45) Date of Patent: Jul. 3, 2018

(54) USING THE LIGHT ADJUSTABLE LENS (LAL) TO INCREASE THE DEPTH OF FOCUS BY INDUCING TARGETED AMOUNTS OF ASPHERICITY

(71) Applicant: RxSight, Inc., Aliso Viejo, CA (US)

(72) Inventors: Christian A. Sandstedt, Pasadena, CA (US); Pablo Artal, Murica (ES); Eloy A. Villegas, Alicante (ES)

(73) Assignee: RxSight, Inc., Aliso Viejo, CA (US)

( * ) Notice: Subject to any disclaimer, the term of this patent is extended or adjusted under 35 U.S.C. 154(b) by 0 days.

(21) Appl. No.: 15/215,579

(22) Filed: Jul. 20, 2016

(65) Prior Publication Data

US 2016/0324629 A1 Nov. 10, 2016

Related U.S. Application Data

(63) Continuation of application No. 13/488,099, filed on Jun. 4, 2012.

(Continued)

(51) Int. Cl.
*A61F 2/16* (2006.01)
*C08J 3/28* (2006.01)
(Continued)

(52) U.S. Cl.
CPC ............ *A61F 2/1635* (2013.01); *A61F 2/164* (2015.04); *A61F 2/1637* (2013.01); *B29C 35/00* (2013.01); *B29D 11/00442* (2013.01); *C08J 3/246* (2013.01); *C08J 3/28* (2013.01); *C08L 83/04* (2013.01); *C08G 77/12* (2013.01);
(Continued)

(58) Field of Classification Search
CPC ...... A61F 2/1635; A61F 2/164; A61F 2/1637; B29D 11/00442; B29C 35/00; C08L 83/04; C08J 3/246; C08J 3/28; C08J 2383/06; C08J 2383/07; C08G 77/12; C08G 77/20
See application file for complete search history.

(56) References Cited

U.S. PATENT DOCUMENTS 4,260,725 A   4/1981   Keogh et al.
4,457,590 A   7/1984   Moore
(Continued)

FOREIGN PATENT DOCUMENTS

CN   1346251   4/2002
CN   1618030   5/2005
(Continued)

OTHER PUBLICATIONS

Camellin and Calossi, (2006) "A new formula for intraocular lens power calculation after refractive corneal surgery," J. Refract. Surg. 22(2): 187-199.

(Continued)

*Primary Examiner* — Mark Eashoo
*Assistant Examiner* — Jessica M Roswell

(57) ABSTRACT

In general, the present invention relates to optical elements, which can be modified post-manufacture such that different versions of the element will have different optical properties. In particular, the present invention relates to lenses, such as intraocular lenses, which can be converted into aspheric lenses post-fabrication. Also, the present invention relates to a method for forming aspheric lenses post-fabrication.

15 Claims, 12 Drawing Sheets

Related U.S. Application Data

(60) Provisional application No. 61/535,793, filed on Sep. 16, 2011.

(51) Int. Cl.

| | | |
|---|---|---|
| *C08L 83/04* | (2006.01) | |
| *C08J 3/24* | (2006.01) | |
| *B29C 35/00* | (2006.01) | |
| *B29D 11/00* | (2006.01) | |
| *C08G 77/12* | (2006.01) | |
| *C08G 77/20* | (2006.01) | |

(52) U.S. Cl.
CPC .......... *C08G 77/20* (2013.01); *C08J 2383/06* (2013.01); *C08J 2383/07* (2013.01)

(56) References Cited

U.S. PATENT DOCUMENTS

| | | | |
|---|---|---|---|
| 5,225,858 | A | 7/1993 | Portney |
| 5,236,970 | A | 8/1993 | Christ et al. |
| 5,278,258 | A | 1/1994 | Gerace et al. |
| 5,376,694 | A | 12/1994 | Christ et al. |
| 5,444,106 | A | 8/1995 | Zhou et al. |
| 6,145,987 | A | 11/2000 | Baude et al. |
| 7,287,852 | B2 | 10/2007 | Fiala |
| 7,350,916 | B2 | 4/2008 | Hong et al. |
| 7,478,907 | B2 | 1/2009 | Somani et al. |
| 7,648,238 | B2 | 1/2010 | Dai et al. |
| 7,950,398 | B2 | 5/2011 | Schroeder et al. |
| 8,109,999 | B2 | 2/2012 | Hampp |
| 8,142,499 | B2 | 3/2012 | Somani et al. |
| 8,307,832 | B2 | 11/2012 | Schroeder et al. |
| 8,529,559 | B2 | 9/2013 | Liang |
| 8,858,541 | B2 | 10/2014 | Liang |
| 2002/0100990 | A1 | 8/2002 | Platt et al. |
| 2002/0122153 | A1 | 9/2002 | Piers |
| 2005/0043794 | A1 | 2/2005 | Geraghty et al. |
| 2005/0187622 | A1* | 8/2005 | Sandstedt ............... A61F 2/16 623/6.22 |
| 2006/0030938 | A1 | 2/2006 | Altmann |
| 2006/0244904 | A1 | 11/2006 | Hong |
| 2006/0244906 | A1 | 11/2006 | Piers |
| 2006/0244916 | A1* | 11/2006 | Guillon ............... A61B 3/103 351/159.75 |
| 2006/0273479 | A1 | 12/2006 | Brait |
| 2007/0260311 | A1 | 11/2007 | Jethmalani et al. |
| 2007/0279585 | A1* | 12/2007 | Bartoli ............... A61F 2/16 351/159.01 |
| 2008/0027537 | A1 | 1/2008 | Gerlach |
| 2008/0231810 | A1 | 9/2008 | Catania |
| 2009/0157178 | A1 | 6/2009 | Hampp |
| 2010/0057202 | A1 | 4/2010 | Bogaert |
| 2010/0165821 | A1 | 7/2010 | Kim et al. |
| 2010/0274234 | A1 | 10/2010 | Liang |
| 2011/0082542 | A1 | 4/2011 | Norrby |
| 2011/0228217 | A1 | 9/2011 | Schroeder et al. |
| 2012/0123534 | A1 | 5/2012 | Yoon et al. |
| 2012/0130486 | A1 | 5/2012 | Yoon |
| 2013/0072591 | A1 | 3/2013 | Sandstedt |

FOREIGN PATENT DOCUMENTS

| | | |
|---|---|---|
| CN | 1873476 | 12/2006 |
| CN | 101793984 | 8/2010 |
| EP | 2202544 | 6/2010 |
| WO | WO 00/41650 | 7/2000 |
| WO | WO 03/058296 | 7/2003 |

OTHER PUBLICATIONS

Chokshi et al., (2007) "Intraocular lens calculations after hyperopic refractive surgery." Ophthalmology. 114: 2044-2049.

Fernandez et al., (2002) "Adaptive Optics Visual Simulator," J. Refract. Surg. 18: S634-S638.

Ellingson., (1990) "Explanation of 3M Diffractive Intraocular Lenses," J. Cataract and Refractive Surgery. 16: 697-702.

Fam and Lim., (2008) "A comparative analysis of intraocular lens power calculation methods after myopic excimer laser surgery," J. Refract. Surg. 24: 355-360.

Feiz et al., (2005) "Nomogram-based intraocular lens power adjustment after myopic photorefractive keratectomy and LASIK," Ophthalmology. 112: 1381-1387.

Hansen et al., (1990) "New Multifocal Intraocular Lens Design," Cataract and Refractive Surgery. 16: 38-41.

Jin et al., (2007) "Intraocular lens exchange due to incorrect lens power," Ophthalmology. 114: 417-424.

Latkany et al., (2005) "Intraocular lens calculations after refractive surgery," J. Cataract and Refractive Surgery. 31: 562-570.

Mackool et al., (2006) "Intraocular lens power calculation after laser in situ keratomileusis; aphakic refraction technique," J. Cataract and Refractive Surgery. 32: 435-437.

Mamalis et al., (2008) "Complications of foldable intraocular lenses requiring explantation or secondary intervention—2007 survey update," J. Cat. & Refract. Surg 34;1584-1591.

Murphy et al., (2002) "Refractive error and visual outcome after cataract extraction," J. Cataract and Refractive Surgery. 28: 62-66.

Narvsez et al., (2006) "Accuracy of intraocular lens power prediction using the Hoffer Q, Holladay 1, Holladay 2, and SRK/T formulas," J. Cat. & Refract. Surg, 32: 2050-2053.

Olsen, (1992) "Sources of error in intraocular-lens power calculation," J. Cataract and Refractive Surgery, 18: 125-129.

Packer et al., (2004) "Intraocular lens power calculation after incisional and thermal keratorefractive surgery," J. Cataract and Refractive Surgery. 30: 1430-1434.

Packer et al., (2002) "Refractive Lens Exchange with the Array Multifocal Intraocular Lens," J. Cataract and Refractive Surgery, 28: 421-424.

Preussner et al., (2004) "Predicting postoperative intraocular lens position and refraction," J. Cataract and Refractive Surgery, 30: 2077-2083.

Steiner et al., (1999) "A Prospective Comparative Study of the AMO Array zonal-progressive multifocal silicone intraocular lens and a monofocal intraocular lens," Ophthalmology. 106: 1243-1255.

Sun et al., (2000) "Toric intraocular lenses for correcting astigmatism in 130 eyes," Ophthalmology. 107: pp. 1776-1781.

Thibos et al., (2004) "Accuracy and Precision of Objective Refraction from Wavefront Aberrations," Journal of Vision. 4: 329-351.

Wang et al., (2004) "Comparison of intraocular lens power calculation methods in eyes that have undergone LASIK," Ophthalmology, 111: 1825-1831.

Reiley et a., (2009) "Ophthalmic applications of the digital micromirror device (DMD)," Proceedings of SPIE, 7210: 721003-1-721003-11.

Piers, et al., "Adaptive Optics Simulation of Intraocular Lenses with Modified Spherical Aberration," IOVS, Dec. 2004, vol. 45, No. 12, pp. 4601-4610.

Charles E. Campbell, "Analysis of wavefront-guided corrections to see if they fully correct ocular aberrations," J. Opt. Soc. Am. A, Jul. 2006, vol. 23, No. 7, pp. 1559-1565.

Pepose et al., "Comparison of contrast sensitivity, depth of field and ocular wavefront aberrations . . . ," Graefes Arch Clin Exp Ophthahnol (2009) 247:965-973.

Cochener, et al., "Comparison of outcomes with multifocal intraocular lenses: a meta-analysis," Clinical Ophthalmology (2011) 5:45-56.

Salmon, et al., "Comparison of the eye's wave-front aberration measured psychophysically and with the . . . ," J. Opt. Soc. Am. A, Sep. 1998, vol. 15, No. 9, pp. 2457-2465.

A. Guirao and P. Artal, "Corneal wave aberration from videokeratography: accuracy and limitations of the Shack . . . ," J. Opt. Soc. Am. A, vol. 17, No. 6, Jun. 2000. pp. 955-965.

Legras et al., "Effect of coma and spherical aberration on depth-of-focus measured using adaptive optics and . . . ," J Cataract Retract Surg, Mar. 2012, vol. 38, pp. 458-469.

(56) References Cited

OTHER PUBLICATIONS

Smith et al., "Effect of defocus on on-axis wave aberration of a centered optical system," J. Opt. Soc. Am. A, Nov. 2006, vol. 23, No. 11, pp. 2686-2689.
G. J. Burton and N. D. Haig, "Effects of the Seidel aberrations on visual target discrimination," J. Opt. Soc. Am. A, Apr. 1984, vol. 1, No. 4, pp. 373-385.
Gross et al., "Human eye," Handbook of Optical Systems: vol. 4 Survey of Optical Instruments. Edited by Herbert Gross, Mar. 2008, pp. 1-87.
K. Shinomori and J. S. Werner, "Impulse response of an S-cone pathway in the aging visual system," J. Opt. Soc. Am. A, Jul. 2006, vol. 23, No. 7, pp. 1570-1577.
Pulaski et al., "Measurement of aberrations in microlenses using a Shack-Hartmann wavefront sensor," Proc. SPIE 4767, Oct. 2002, pp. 1-9.
Valdemar Portney, "New Bi-Sign Aspheric IOL and Its Application," Optometry and Vision Science, vol. 89, No. 1, Jan. 2012, pp. 1-10.
Young et al., "Not all aberrations are equal: Reading impairment depends on aberration type and magnitude," Journal of Vision, Nov. 2011, 11(13):20, pp. 1-19.
Barbero et al., "Optical aberrations of intraocular lenses measured in vivo and in vitro," J. Opt. Soc. Am. A, vol. 20, No. 10, Oct. 2003, pp. 1841-1851.
Wang et al., "Optical aberrations of the human anterior cornea," J Cataract Refract Surg, vol. 29, Aug. 2003, pp. 1514-1521.
Werner et al., "Spherical aberration yielding optimum visual performance: Evaluation of intraocular lenses . . . ," J Cataract Refract Surg, vol. 35, Jul. 2009, pp. 1229-1233.
D. A. Atchison and H. Guo, "Subjective Blur Limits for Higher Order Aberrations," Optometry and Vision Science, vol. 87, No. 11, Nov. 2010, pp. E890-E898.
G. Smith and D. A. Atchison, "The gradient index and spherical aberration of the lens of the human eye," Ophthal. Physiol. Opt., vol. 21, No. 4, Jul. 2001, pp. 317-326.
Applegate et al., "Visual Acuity as a Function of Zernike Mode and Level of Root Mean Square Error," Optometry and Vision Science, vol. 80, No. 2, Feb. 2003, pp. 97-105.
Holladay et al., "A New Intraocular Lens Design to Reduce Spherical Aberration of Pseudophakic Eyes," Journal of Refractive Surgery, vol. 18, Nov./Dec. 2002, pp. 683-692.
Montes-Mico et al., "Analysis of the possible benefits of aspheric intraocular lenses: Review-of the literature," J Cataract Refract Surg, vol. 35, Jan. 2009, pp. 172-181.
H.-L. Liou and N. A. Brennan, "Anatomically accurate, finite model eye for optical modeling," J. Opt. Soc. Am. A, vol. 14, No. 8, Aug. 1997, pp. 1684-1695.
J. C. Wyant and K. Creath, "Basic Wavefront Aberration Theory for Optical Metrology," Applied Optics and Optical Engineering, vol. XI, 1992, pp. 1-12.
D. D. Koch and L. Wang, "Custom Optimization of Intraocular Lens Asphericity," Trans Am Ophthalmol Soc, vol. 105, 2007, pp. 36-42.
Buckhurst et al., "Development of a questionnaire to assess the relative subjective benefits of presbyopia correction," J Cataract Refract Surg, vol. 38, Jan. 2012, pp. 74-79.
Kay et al., "Extended depth of field by colored apodization," Optics Letters, vol. 36, No. 23, Dec. 1, 2011, pp. 4614-4616.
Zheleznyak et al., "Impact of corneal aberrations on through-focus image quality of presbyopia-correcting . . . ," J Cataract Refract Surg, vol. 38, Oct. 2012, pp. 1724-1733.
Applegate et al., "Interaction between aberrations to improve or reduce visual performance," J Cataract Refract Surg, vol. 29, Aug. 2003, pp. 1487-1495.
Atchison et al., "Limits of spherical blur determined with an adaptive optics mirror," Ophtha. Physio. Opt., vol. 29, No. 3, 2009, pp. 300-311.
Norrby et al., "Model eyes for evaluation of intraocular lenses," Applied Optics, vol. 46, No. 26, Sep. 2007, pp. 6595-6605.
Liang et al., "Objective measurement of wave aberrations of the human eye with the use of a Hartmann-Shack . . . ," J. Opt. Soc. Am. A, vol. 11, No. 7, Jul. 1994, pp. 1949-1957.
Iskander et al., "Objective refraction from monochromatic wavefront aberrations via Zernike power polynomials," Ophthal. Physiol. Opt., vol. 27, 2007, pp. 245-255.
Guirao et al., "Optical aberrations of the human cornea as a function of age," J. Opt. Soc, Am. A, vol. 17, No. 10, Oct. 2000, pp. 1697-1702.
Schwiegerling et al., "Representation of videokeratoscopic height data with Zernike polynomials," J. Opt. Soc. Am. A, vol. 12, No. 10, Oct. 1995, pp. 2105-2113.
Sicam et al., "Spherical aberration of the anterior and posterior surfaces of the human cornea," J. Opt. Soc. Am. A, vol. 23, No. 3, Mar. 2006, pp. 544-549.
Zhao et al., "Spherical Aberrations of Human Astigmatic Corneas," Journal of Refractive Surgery, vol. 27, No. 11, 2011 , pp. 846-848.
Thibos et al., "Standards for Reporting the Optical Aberrations of Eyes," OSA TOPS, vol. 35 Vision Science and Its Applications, 2000, pp. 232-244.
Thibos et al., "Statistical variation of aberration structure and image quality in a normal," J. Opt. Soc. Am. A, vol. 19, No. 12, Dec. 2002, pp. 2329-2348.
Kollbaum, et al., "Validation of an Off-Eye Contact Lens Shack-Hartmann Wavefront Aberrometer," Optometry and Vision Science, vol. 85, No. 9, Sep. 2008, pp. E817-E828.
Cheng et al., "Visual Impact of Zernike and Seidel Forms of Monochromatic Aberrations," Optometry and Vision Science, vol. 87, No. 5, May 2010, pp. 301-312.
Villegas, et al., "Extended Depth of Focus With Induced Spherical Aberration in Light-Adjustable Intraocular Lenses," American Journal of Ophtalmology, Jan. 2014, pp. 142-149.
Bará, et al, "Estimating the eye aberration coefficients in resited pupils: is it better to refit or to resoale?" J. Opt. Soc. Am. A, vol. 31, No. 1. Jan. 2014, pp. 114-123.

\* cited by examiner

USING THE LIGHT ADJUSTABLE LENS (LAL) TO INCREASE THE DEPTH OF FOCUS BY INDUCING TARGETED AMOUNTS OF ASPHERICITY

CROSS REFERENCE TO RELATED APPLICATIONS

This application is a continuation of and therefore claims benefit from U.S. patent application Ser. No.: 13/488,099, filed on Jun. 4, 2012, which claims benefit from U.S. Provisional Application No.: 61/535,793 filed on Sep. 16, 2011, both applications incorporated herein by reference in their entirety.

TECHNICAL FIELD

The field of the invention includes at least medical and surgical instruments; treatment devices; surgery and surgical supplies; and, medicine. In general, the field of subject matter of the invention includes ophthalmology. More specifically, the disclosure relates to optical elements, which can be modified post-manufacture such that different versions of the element will have different optical properties. In particular, the disclosure relates to lenses, such as intraocular lenses, which can be converted into aspheric lenses post-fabrication.

BACKGROUND OF THE INVENTION

An intraocular lens (IOL) is a surgically implanted, polymeric lens designed to replace the natural crystalline lens in the human eye, typically in patients who have developed visually significant cataracts. Since their inception in the late 1940's, IOLs have provided improved uncorrected visual acuity (UCVA) compared to that of the cataractous or aphakic state; however, problems in predictably achieving emmetropia persist as most post-cataract surgery patients rely on spectacles or contact lenses for optimal distance vision. Compounding the issues related to achieving optimum distance vision, patients undergoing cataract surgery lose their ability to accommodate, i.e. the ability to see objects at both near and distance.

The determination of IOL power required for a particular post-operative refraction is dependent on the axial length of the eye, the optical power of the cornea, and the predicted location of the IOL within the eye. Accurate calculation of IOL power is difficult because the determination of axial length, corneal curvature, and the predicted position of the IOL in the eye is inherently inaccurate. (Narvaez el al., 2006; Olsen, 1992; Preussner et al., 2004; Murphy et al., 2002). Surgically induced cylinder and variable lens position following implantation will create refractive errors, even if preoperative measurements were completely accurate. (Olsen, 1992) Currently, the options for IOL patients with less than optimal uncorrected vision consist of post-operative correction with spectacles, contact lenses or refractive surgical procedures. Because IOL exchange procedures carry significant risk, secondary surgery to remove the IOL and replace the first IOL with a different power IOL is generally limited to severe post-operative refractive errors.

With current methods of IOL power determination, the vast majority of patients achieve a UCVA of 20/40 or better. A much smaller percentage achieves optimal vision without spectacle correction. Nearly all patients are within two diopters (D) of emmetropia.

In a study of 1,676 patients, 1,569 (93.6%) patients were within two diopters of the intended refractive outcome. (Murphy el al., 2002). In 1,320 cataract extractions on patients without ocular co-morbidity, Murphy and co-workers found that 858 (65%) had uncorrected visual acuity greater than 20/40. (Murphy et al., 2002). A 2007 survey of cataract surgeons reported that incorrect IOL power remains a primary indication for foldable IOL explanation or exchange. (Mamalis et al., 2008; and Jin et al., 2007)

In addition to imprecise IOL power determinations, post-operative uncorrected visual acuity is most often limited by pre-existing astigmatism, Staar Surgical (Monrovia, Calif.) and Alcon Laboratories (Ft. Worth, Tex.) both market a toric IOL that corrects pre-existing astigmatic errors. These IOLs are available in only two to three tone powers (2.0, 3.5 D and 1.50, 2.25 and 3.0 D, respectively at the IOL plane) and the axis must be precisely aligned at surgery. Other than surgical repositioning, there is no option to adjust the IOL's axis which may shift post-operatively. (Sun et al., 2000) Furthermore; individualized correction of astigmatism is limited by the unavailability of multiple toric powers.

An additional problem associated with using pre-implantation corneal astigmatic errors to gauge the required axis and power of a toric IOL is the unpredictable effect of surgical wound healing on the final refractive error. After the refractive effect of the cataract wound stabilizes, there is often a shift in both magnitude and axis of astigmatism which off-sets the corrective effect of a toric IOL. Therefore, a means to postoperatively adjust (correct) astigmatic refractive errors after lens implantation and surgical wound healing is very desirable. While limbal relaxing incision is a widely accepted technique for treating corneal astigmatism, the procedure is typically performed during cataract surgery; therefore, the procedure does not address the effect of post-implantation wound healing.

In the United States alone, approximately one million eyes undergo corneal refractive procedures which subsequently develop cataracts, thus, presenting a challenge with respect to IOL power determination. Corneal topographic alterations induced by refractive surgery reduce the accuracy of keratometric measurements, often leading to significant post-operative ametropia. (Feiz et al., 2005; Wang et al., 2004; Latkany et al., 2005, Mackool et al., 2006; Packer et al., 2004; Fam and Lim, 2008, Chokshi et al., 2007, Camellin and Calossi, 2006). Recent studies of patients who have had corneal refractive surgery (photorefractive keratectomy, laser in situ keratomileusis, radial keratotomy) and subsequently required cataract surgery frequently demonstrate refractive "surprises" post operatively. As the refractive surgery population ages and develops cataracts, appropriate selection of IOL power for these patients has become an increasingly challenging clinical problem. The ability to address this problem with an adjustable IOL is valuable to patients seeking optimal distance vision after cataract surgery.

Accommodation, as it relates to the human visual system, refers to the ability of a person to use their unassisted ocular structure to view objects at both near (e.g. reading) and far (e.g. driving) distances. The mechanism whereby humans accommodate is by contraction and relaxation of the ciliary body, which connects onto the capsular bag surrounding the natural lens. Under the application of ciliary stress, the human lens will undergo a shape change effectively altering the radius of curvature of the lens. (Ciuffreda, 1998). This action produces a concomitant change in the power of the lens. However, as people grow older the ability for their eyes to accommodate reduces dramatically. This condition is known as presbyopia and currently affects more than 90 million people in the United States. The most widely accepted theory to explain the loss of accommodation was put forth by Helmholtz. According to Helmholtz, as the patient ages, the crystalline lens of the human eye becomes progressively stiffer prohibiting deformation under the applied action of the ciliary body. (Helmholtz, 1969). People who can see objects at a distance without the need for spectacle correction, but have lost the ability to see objects up close are usually prescribed a pair of reading glasses or magnifiers. For those patients who have required previous spectacle correction due to preexisting defocus and/or astigmatism, they are prescribed a pair of bifocals, trifocals, variable, or progressive focus leases which allows the person to have both near and distance vision. Compounding this condition is the risk of cataract development as the patient ages.

To effectively treat both presbyopia and cataracts, the patient can be implanted with a multifocal IOL. The two most widely adopted multifocal IOLs currently sold in the United States are the ReZoom® (Abbott Medical Optics, Santa Ana, Calif.) and ReStor® (Alcon, Fort Worth, Tex.) lenses. The ReZoom® lens is comprised of five concentric, aspheric refractive zones, (U.S. Pat. No. 5,225,858). Each zone is a multifocal element and thus pupil size should play little or no role in determining final image quality. However, the pupil size must be greater than 2.5 mm to be able to experience the multifocal, effect. Image contrast is sacrificed at the near and for distances, to achieve the intermediate and has an associated loss equivalent to one line of visual acuity, (Steiner et al., 1999). The ReStor® lenses, both the 3.0 and 4.0 versions, provide simultaneous near and distance vision by a series of concentric, apodized diffractive rings in the central, three millimeter diameter of the lenses. The mechanism of diffractive optics should minimize the problems associated with variable pupil sizes and small amounts of dec-entration. The acceptance and implantation of both of these lenses has been limited by the difficulty experienced with glares, rings, halos monocular diplopia, and the contraindication for patients with an astigmatism of greater than or equal to 2.0 D. (Hansen et al., 1990; and, Ellingson, 1990). Again precise, preoperative measurements and accurate IOL power calculations are critical, to the success of the refractive outcome, and neither the ReZoom nor the ReStor lenses provide an opportunity for secondary power adjustment post implantation. (Packer et al., 2002).

One of the newest concepts proposed to tackle the dual problems of cataract's and presbyopia are through the use of accommodating IOLs. Two companies, Bausch & Lomb (Rochester, N.Y.) and Human Optics AG (Erlangen, Germany) have developed IOLs that attempt to take advantage of the existing accommodative apparatus of the eye in post implantation patients to treat presbyopia. Bausch & Lomb's lens offers a plate haptic configured IOL with a flexible hinged optic (CrystaLens®). Human Optics's lens (AK-KOMMODATIVE® ICU) is similar in design, but possesses four hinged haptics attached to the edge of the optic. The accommodative effect of these lenses is caused by the vaulting of the plate IOL by the contraction of the ciliary body. This vaulting may be a response of the ciliary body contraction directly or caused by the associated anterior displacement of the vitreous body. Initial reports of the efficacy of these two lenses in clinical trials was quite high with dynamic wavefront measurement data showing as much as 2 D to 3 D (measured at the exit pupil of the eye) of accommodation. However, the FDA Ophthalmic Devices' panel review of Bausch & Lomb's clinical results concluded that only a 1 D accommodative response (at the spectacle plane) was significantly achieved by their lens, which is nearly identical to the pseudo-accommodation values achieved for simple monofocal IOLs.

A need exists for an intraocular lens which is adjusted post operatively in-vivo to form a presbyopia correcting intraocular lens. This type of lens can be designed in-vivo to correct to an initial emmetropic state (light from infinity forming a perfect focus on the retina) and then the presbyopia correction is added during a second treatment. Such a lens would (1) remove the guess work involved in presurgical power selection, (2) overcome the wound healing response inherent to IOL implantation, and (3) allow the amount of near vision to be customized to correspond to the patient's requirements. Also, an intraocular lens which is adjusted post operatively in-vivo to form an aspheric optical element would result in the patient having an increased depth of focus (DOF), which allows the patient to see both distance and near (e.g. 40 cm) through the same lens.

BRIEF SUMMARY OF THE INVENTION

General embodiments of the present invention provide a first optical element whose properties may be adjusted post-manufacture to produce a second optical element, wherein the second optical element is capable of providing an increased depth of focus to a patient. Specifically, the invention relates to a spherical intraocular lens that is capable of being transformed post-operatively into an aspheric optical element. Through this approach, the intraocular and/or focal zones of the aspheric optical element can be more precisely adjusted after the lens has been subjected to any post-operative migration. Also, the adjustment of the aspheric optical element can be based on input from the patient and/or the adjustment of the aspheric optical element can be accomplished through standard retraction techniques rather than making the adjustment through pre-operative estimation.

The alteration of the spherical IOL is accomplished via a modifying composition ("MC") dispersed throughout the spherical IOL. The MC is capable of polymerization when exposed to an external stimulus such as heat or-light. The stimulus can be directed to one or more regions of the element causing polymerization of the MC only in the exposed regions. The polymerization of the MC causes changes in the optical properties of the element within the exposed regions. In some embodiments, the optical properties changed though the polymerization of the MC include a change in the radius of curvature and/or a change in the refractive index.

The method for providing an aspheric lens begins with the formation of the first polymer matrix in the presence of the modifying composition. The next step is the formation of a second polymer matrix comprising polymerized MC. The formation of this polymer network changes the optical properties of the element, namely the refractive index. In addition, when the MC is polymerized to form the second polymer matrix, a gradient or a difference in the chemical potential between the polymerized and unpolymerized regions is induced. This in turn causes the unpolymerized MC to diffuse within the element, which reestablishes a thermodynamic equilibrium within the optical element. If the optical element possesses sufficient elasticity, this migration of MC can cause swelling of the element in the area exposed to the stimulus. This, in turn, changes the shape of the element, causing changes in the optical, properties (i.e., radius of curvature and/or refractive index). Whether the radius of curvature of the element and/or the refractive index of the dement change depends upon (1) the nature of the optical element, (2) the MC incorporated into the element, (3) the duration that the element is exposed to a stimulus, and (4) the spatial intensity profile of the stimulus.

By controlling the radiant exposure (i.e., beam irradiance and duration), spatial irradiance profile, and target area, physical changes in the radius of curvature of the lens surface are achieved, thereby modifying the refractive power of an implanted lens (1) to correct spherical refractive errors, (2) to correct sphero-cylindrical refractive errors, (3) to induce a targeted amount of asphericity and/or a combination thereof. Once the appropriate refractive adjustment is achieved, the entire aspheric lens is irradiated to polymerize the remaining unreached MC under conditions that prevent any additional change in lens power. By irradiating the entire lens, MC diffusion is prevented thus no change in lens power results. This second irradiation procedure is referred to as "lock-in".

In another aspect of the present invention, the optical elements are self-contained in that once fabricated, no material is either added or removed from the lens to obtain the desired optical properties.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing.

DETAILED DESCRIPTION OF THE INVENTION

Figure 1:
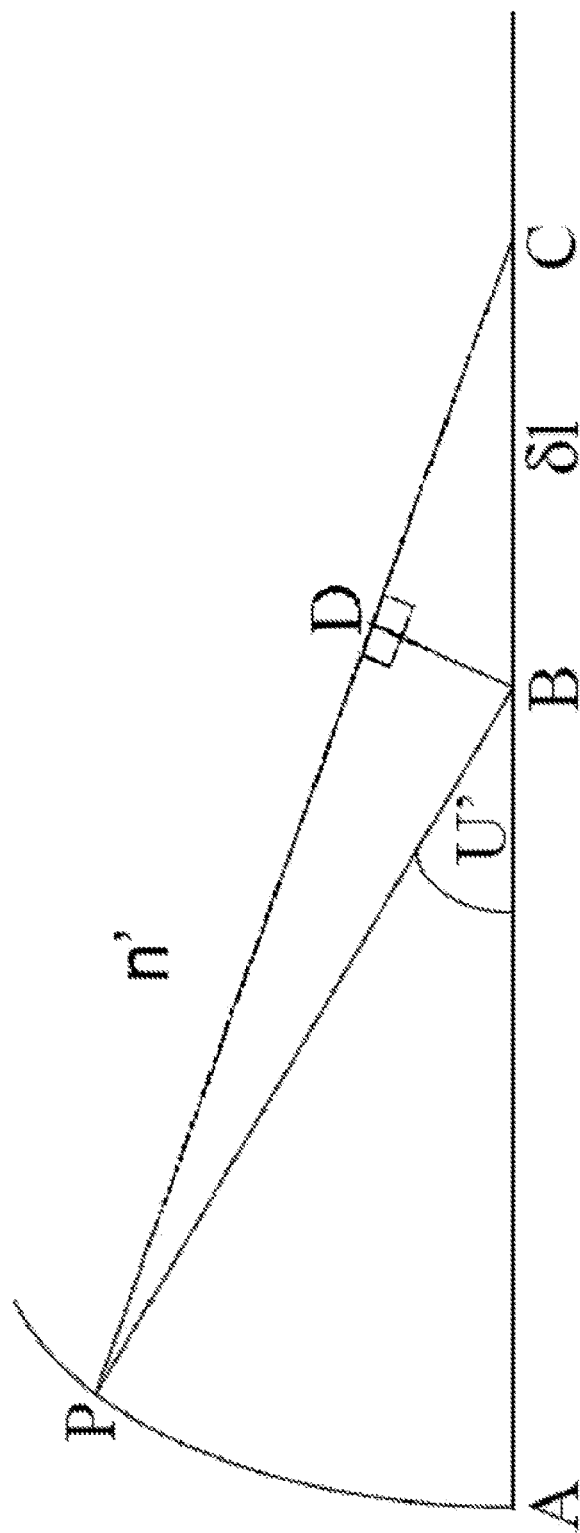
FIG. 1 shows a schematic representation of the depth of focus.

As used herein the specification, "a" or "an" may mean one or more. As used herein in the claim(s), when used in conjunction with the word "comprising", the words "a" or "an" may mean one or more than one. As used herein "another" may mean, at least a second or more. Furthermore, as used herein, the terms "comprise," "have" and "include" are open-ended linking verbs. Any forms or tenses of one or mote of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

Throughout this application, the term "about" is used to indicate that a value includes the inherent variation of error for the device, the method being employed to determine the value, or the variation that exists among the experimental test articles.

Chemical Group Definitions

When used in the context of a chemical group, "hydrogen" means —H; "hydroxy" means —OH; "oxo" means =O; "halo" means independently —F, —Cl, —Br or —I; "amino" means —NH$_2$ (see below for definitions of groups containing the term amino, e.g., alkylamino); "hydroxyamino" means —NHOH; "nitro" means —NO$_2$; imino means =NH (see below for definitions of groups containing the term imino, e.g., alkylimino); "cyano" means —CN; "isocyanate" means —N=C=O; "azido" means —N₃; in a monovalent context "phosphate" means —OP(O)(OH)₂ or a deprotonated form thereof; in a divalent context "phosphate" means —OP(O)(OH)O— or a deprotonated form thereof; "mercapto" means —SH; and "this" means =S.

In the context of chemical formulas, the symbol "—" means a single bond, "=" means a double bond, and "≡" means triple bond. The symbol "----" represents an optional bond, which if present is either single or double. The symbol "⇌" represents a single bond or a double bond. Thus, for example, the structure

includes the structures

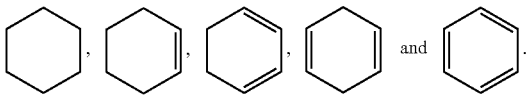

As will be understood by a person of skill in the art, no one such ring atom forms part of more than one double bond. The symbol "〰", when drawn perpendicularly across a bond indicates a point of attachment of the group. It is noted that the point of attachment is typically only identified in this manner for larger groups in order to assist the reader in rapidly and unambiguously identifying a point of attachment. The symbol "◄" means a single bond where the group attached to the thick end of the wedge is "out of the page." The symbol "◁" means a single bond where the group attached to the thick end of the wedge is "into the page". The symbol "〰" means a single bond where the conformation (e.g., either R or S) or the geometry is undefined (e.g., either E or Z).

Any undefined valency on an atom of a structure shown in this application implicitly represents a hydrogen atom bonded to the atom. When a group "R" is depicted as a "floating group" on a ring system, for example, in the formula:

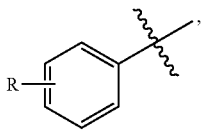

then R may replace any hydrogen atom attached to any of the ring atoms, including a depicted implied, or expressly defined hydrogen, so long as a stable structure is formed. When a group "R" is depicted as a "floating group" on a fused ring system, as for example in the formula:

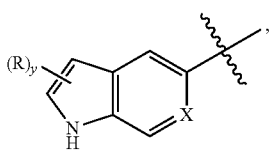

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "saturated" as used herein means the compound or group so modified has no carbon-carbon double and no carbon-carbon triple bonds, except as noted below. The term does not preclude carbon-heteroatom multiple bonds, for example a carbon oxygen double bond or a carbon nitrogen double bond. Moreover, it does not preclude a carbon-carbon double bond that may occur as part of keto-enol tautomerism or imine/enamine tautomerism.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl). When the term "aliphatic" is used without the "substituted" modifier only carbon and hydrogen atoms are present. When the term is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂.

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl. The groups —CH₃ (Me), —CH₂CH₃ (Et), —CH₂CH₂CH₃ (n-Pr), —CH(CH₃)₂ (iso- Pr), —CH(CH$_2$)$_2$ (cyclopropyl), —CH$_2$CH$_2$CH$_2$CH$_3$ (nBu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and

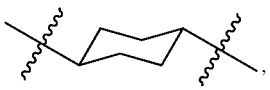 [SMILES: *C1CCC(*)CC1]

are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH$_2$, =CH(CH$_2$CH$_3$), and =C(CH$_3$)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen has been substituted with a halo group and no other atoms aside from carbon, hydrogen and halogen are present. The group, —CH$_2$Cl is a non-limiting examples of a haloalkyl. An "alkane" refers to the compound H—R, wherein R is alkyl. The term "fluoroalkyl" is a subset of substituted alkyl, in which one or more hydrogen has been substituted with a fluoro group and no other atoms aside from carbon, hydrogen and fluorine are present. The groups, —CH$_2$F, —CF$_3$, and —CH$_2$CF$_3$ are non-limiting examples of fluoroalkyl groups. An "alkane" refers to the compound H—R, wherein R is alkyl.

The term "alkenyl" when used without the "substituted" modifier refers to an monovalent unsaturated aliphatic group with a carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CH—C$_6$H$_5$. The term "alkenediyl" when used without the "substituted" modifier refers to a divalent unsaturated aliphatic group, with two carbon atoms as points of attachment, a linear or branched, cyclo, cyclic or acyclic structure, no carbon-carbon double bond, no carbon-carbon triple bonds, and no atoms other than carbon and hydrogen. The groups, —Cl=CH—, —CH=C(CH$_3$)CH$_2$—, —CH=CHCH$_2$—, and

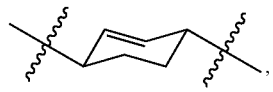

are non-limiting examples of alkenediyl groups. When these terms are used with the "substituted" modifier one or more hydrogen atom has been independently replaced by —OH, —F, —Cl, —Be, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups, —CH=CHF, —CH=CHCl and —CH=CHBr, are non-limiting examples of substituted alkenyl groups. An "alkene" refers to the compound H—R, wherein R is alkenyl.

The term "alkynyl" when used without the "substituted" modifier refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH$_3$, and 13 CH$_2$C≡CCH$_3$, are non-limiting examples of alkynyl groups. The term "alkynediyl" when used without the "substituted" modifier refers to a divalent unsaturated aliphatic group, with two carbon atoms as points of attachment, a linear or branched, cyclo, cyclic or acyclic structure, at least one carbon-carbon triple bond, and no atoms other than carbon and hydrogen. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. An "alkyne" refers to the compound H—R, wherein R is alkynyl.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl group (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and the monovalent group derived from biphenyl. The term "arenediyl" when used without the "substituted" modifier refers to a divalent aromatic group, with two aromatic carbon atoms as points of attachment, said carbon atoms forming part of one or more six-membered. aromatic ring structures) wherein the ring atoms are all carbon, and wherein the monovalent group consists of no atoms other than carbon and hydrogen. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of arenediyl groups include:

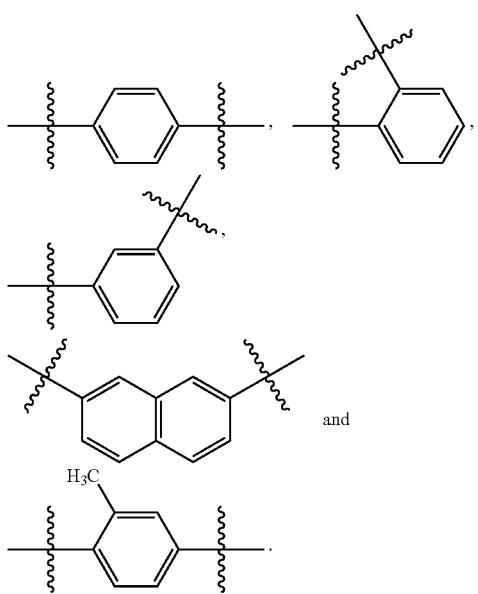

and

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. An "arene" refers to the compound H—R, wherein R is aryl The term "aralkyl" when used without the "substituted" modifier refers to the monovalent group -alkanediyl-aryl, in which the terms, alkanediyl and aryl are each used in a manner consistent with the definitions provided above. Non-limiting examples of aralkyls are: phenylmethyl (benzyl, Bn) and 2-phenyl-ethyl. When the term is used with the "substituted" modifier one or more hydrogen atom from the alkanediyl and/or the aryl has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the group consists of no atoms other than carbon, hydrogen, aromatic nitrogen, aromatic oxygen and aromatic sulfur. As used herein, the term does not preclude the presence of one or more alkyl group (carbon number limitation permitting) attached to the aromatic ring or any additional aromatic ring present. Non-limiting examples of heteroaryl groups include furanyl, imidazolyl, indolyl, indazolyl (Im), methylpyridyl, oxazolyl, pyridyl, pyrrolyl, pyrimidyl, pyrazinyl, quinolyl, quinazolyl, quinoxalinyl, thienyl, and triazinyl. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. As used herein, the term does not preclude the presence of one or more alkyl group (carbon number limitation permitting) attached to the first aromatic ring or any additional aromatic ring present. If more than one ring is present the rings may be fused or unfused. Non-limiting examples of heteroarenediyl groups include:

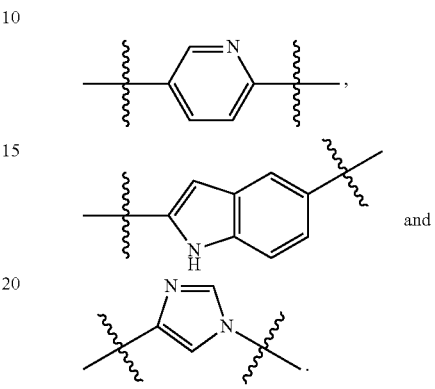

and

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "acyl" when used without the "substituted" modifier refers to the group —C(O)R, in which R is a hydrogen, alkyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. When either of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups, —C(O)CH$_2$CF$_3$, —CO$_2$H (carboxcyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH$_3$, —OCH$_2$CH$_3$, —OCH$_2$CH$_2$CH$_3$, —OCH(CH$_3$)$_2$, —OCH(CH$_2$)$_2$, —O-cyclopentyl, and —O-cyclohexyl. The terms "alkenyloxy" "alkynyloxy", "aryloxy", "aralkoxy", "heteroaryloxy", and "acyloxy", when used without the "substituted" modifier, refers to groups, defined as —OR, in which R is alkenyl, alkynyl, aryl, aralkyl, heteroaryl, and acyl, respectively. Similarly, the term "alkylthio" when used without the "substituted" modifier refers to the group —SR, in which R is an alkyl, as that term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The term "alcohol" corresponds to an alkane, as defined above, wherein at least one of the hydrogen atoms has been replaced with a hydroxy group.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "alkenylamino", "alkynylamino", "arylamino", "aralkylamino", "heteroarylamino", and "alkylsulfonylamino" when used without the "substituted" modifier, refers to groups, defined as —NHR, in which R is alkoxy, alkenyl, alkynyl, aryl, aralkyl, heteroaryl, and alkylsulfonyl, respectively. A non-limiting example of an arylamino group is —NHC$_6$H$_5$. The term, "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. When any of these terms is used with the "substituted" modifier one or more hydrogen atom, has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups —NHC(O)OCH$_3$ and —NHC(O)NHCH$_3$ are non-limiting examples of substituted amido groups.

The term "alkylphosphate" when used without the "substituted" modifier refers to the group —OP(O)(OH)(OR)l in which R is an alkyl, as that term is defined above. Non-limiting examples of alkylphosphate groups include: —OP(O)(OH)(OMe) and —OP(O)(OH)(OEt). The term "dialkylphosphate" when used without the "substituted" modifier refers to the group —OP(O)(OR)(OR'), in which R and R' can be the same or different alkyl. groups, or R and R' can be taken together to represent an alkanediyl. Non-limiting examples of dialkylphosphate groups include: —OP(O)(OMe)$_2$, —OP(O)(OEt)(OMe) and —OP(O)(OEt)$_2$. When any of these terms, is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The terms "alkylsulfonyl" and "alkylsulfinyl" when used without the "substituted" modifier refers to the groups —S(O)$_2$R and —S(O)R, respectively, in which R is an alkyl, as that term is defined above. The terms "alkenylsulfonyl", "alkynylsulfonyl", "arylsulfonyl", "aralkylsulfonyl", and "heteroarylsulfonyl", are defined in an analogous manner. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "effective," as that term is used in the specification and/or claims, means adequate to accomplish a desired, expected, or intended result. "Effective amount," or "Therapeutically effective amount" when used in the context of treating a patient or subject with a stimulus means that the amount; of the stimulus which, when administered, to a subject or patient for treating a condition, is sufficient to effect such treatment for the condition.

As used herein, the term "patient" or "subject" refers to a living mammalian organism, such as a human, monkey, cow, sheep, goat, dog, cat, mouse, rat, guinea pig, or transgenic species thereof, in certain, embodiments, the patient or subject is a primate. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

A "repeat, unit" is the simplest structural entity of certain materials, for example, frameworks and/or polymers, whether organic, inorganic or metal-organic. In the case of a polymer chain, repeat units are linked together successively along the chain, like the beads of a necklace. For example, in polyethylene, —[—CH$_2$CH$_2$—]$_n$—, the repeat unit is —CH$_2$CH$_2$—. The subscript "n" denotes the degree of polymerization, that is, the number of repeat units linked together. When the value for "n" is left undefined or where "n" is absent, it simply designates repetition of the formula within the brackets as well as the polymeric nature of the material. The concept of a repeat unit applies equally to where the connectivity between the repeat units extends three dimensionally, such as in, modified polymers, thermosetting polymers, etc.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

The above definitions supersede any conflicting definition in any of the reference that is incorporated by reference herein. The tact that certain terms are defined, however, should not be considered as indicative that any term that is undefined is indefinite. Rather, all terms used are believed to describe the invention in terms such that one of ordinary skill can appreciate the scope and practice the present invention.

Compositions of the Invention

Compositions of the present disclosure may be made using the methods described above and in Example 1 below. These methods can be further modified and optimized using the principles and techniques of organic chemistry and/or polymer chemistry as applied by a person skilled in the art. Such principles and techniques are taught, for example, in *March's Advanced Organic Chemistry: Reactions, Mechanisms, and Structure* (2007), and/or in R. J. Young & P. A. Lovell, *Introduction to Polymers*, (Chapman & Hall 1991), which are incorporated by reference herein.

Discussion of General Embodiments

From a pure optical standpoint, the depth of focus (DOF) for an optical system (e.g. the eye) is simply defined as the maximum movement away from the ideal image plane, which may be made without causing a serious deterioration of the image. According to the Rayleigh limit, there will be no appreciable deterioration of the image, i.e., no marked change from the Airy pattern, provided the maximum phase difference between disturbances arriving at the center of the pattern, does not exceed π/2. With reference to FIG. 1, this is mathematically stated as:

$$\delta l = \pm \frac{\lambda}{8_{n'sin^2}\frac{U'}{2}}$$

where AP represents a spherical wave converging to the image point B, λ is the wavelength, n' is the refractive index in the image space, U' is the slope of the refracted ray, and δ1 is the DOF. Therefore, an optical system such as the human eye will have an inherent amount of depth of focus even for a perfectly imaging system.

Figure 2:
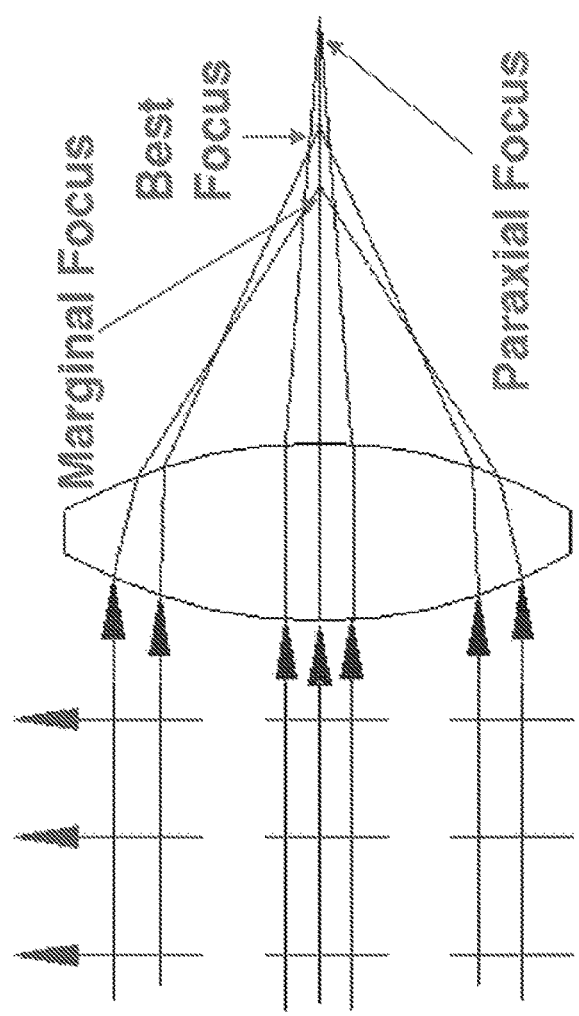
FIG. 2 shows a collimated beam of light being refracted by a spherical lens.

An additional property of optical systems that can be exploited to further increase the depth of focus, and therefore provide for both distance and near vision, is spherical aberration. In simple terms, spherical aberration is defined as the variation of focus with aperture. FIG. 2 graphically depicts a collimated beam of light being refracted by a spherical biconvex lens. Notice that the rays closest to the optical axis come to a focus close to the paraxial focus position. As the ray height at the lens increases, the position of the ray's intersection with the optical axis moves farther and farther away from the paraxial focus. The distance from the paraxial focus to the axial intersection of the ray is called longitudinal spherical aberration. The image of a point formed by a lens with spherical aberration is usually a bright dot surrounded by a halo of light. The effect of spherical aberration on an extended image is to soften the contrast of the image and blur its details. However, it should be possible to induce a specific spherical aberration that increases the depth of focus such that the softening of the focus and the image contrast is acceptable.

Figure 3:
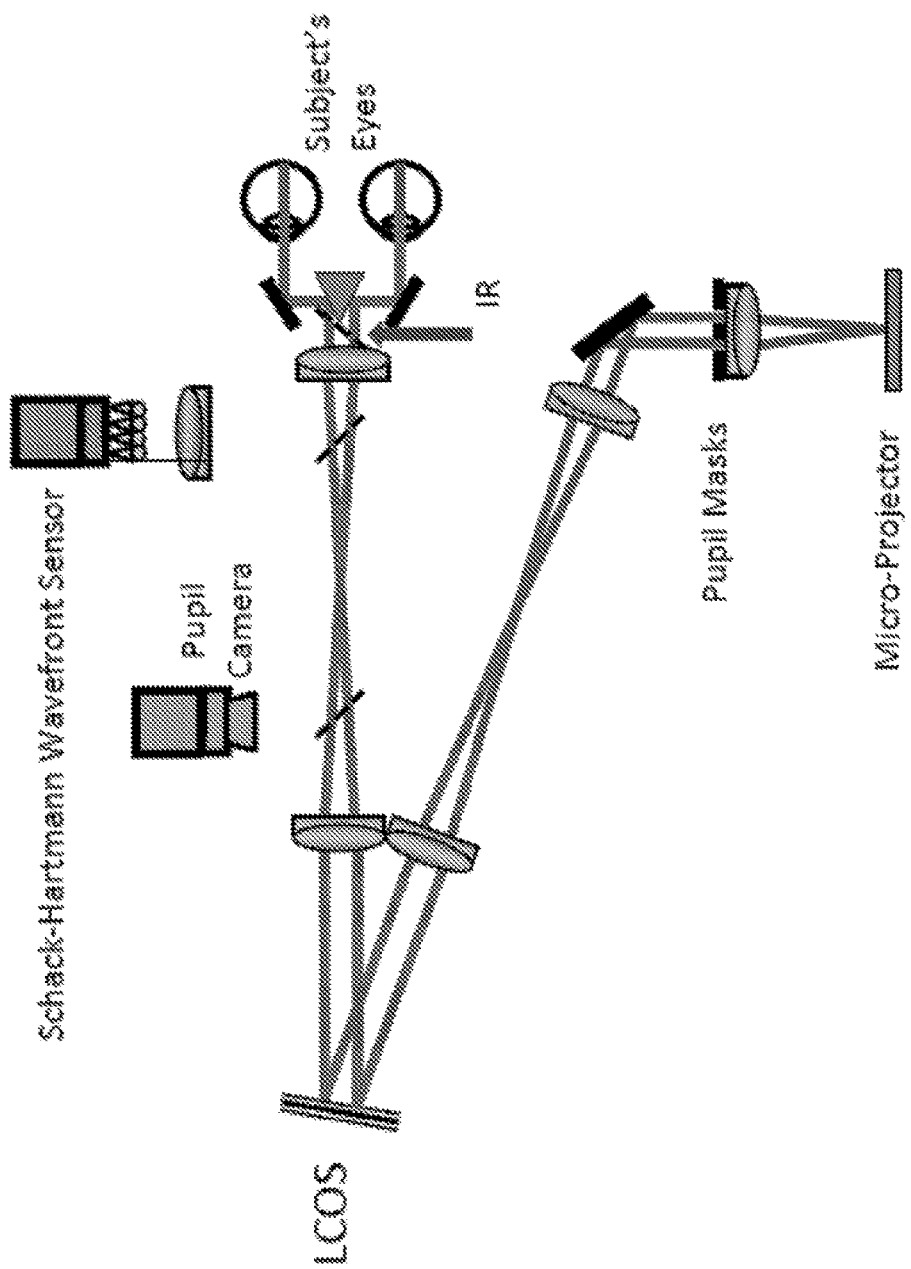
FIG. 3 shows a schematic of the adaptive optics simulator used to determine the optimized values for $4^{th}$ order spherical aberration and defocus.

The presence of spherical aberration increases the depth of focus in the eye. In combination with a residual refractive error (defocus), an induced spherical aberration can be used to provide patients with good contrast images both for distance and near objects. The key issue is to determine the required values of both $4^{th}$ order spherical aberration and defocus that provide good near vision without deteriorating the image quality for distance objects. An experimental, approach that permits determination of the optimum values of spherical aberration and defocus is an adaptive optics visual simulator. (Fernandez et al., 2002). An example of this type of instrument is shown in FIG. 3. This instrument consists of a wavefront sensor (Shack-Hartmann wavefront sensor), a wavefront corrector (Liquid Crystal on Silicon (LCOS)), and an additional optical path to present letters, e.g., a tumbling E, to the subjects under test. The visual acuity of several subjects was measured using a similar setup as that shown in FIG. 3. The visual acuity of the subjects was measured through simulations that consisted of a number of different combinations of residual defocus and spherical aberration measurements for letter objects placed at distances from 30 cm to distance emmetropia. The results of these simulations indicate that the optimum values of negative spherical aberration and defocus to maintain good vision between 40 cm and distance emmetropia are −0.125 μm of $4^{th}$ order spherical aberration in combination with −1.0 D of defocus.

The spherical IOL of the present invention is capable of post-fabrication alteration of optical properties. The lens is self-contained and does not require the addition or removal of materials to change the optical properties. Instead, the optical properties of the lens are altered by exposing a portion or portions of the lens to an external stimulus which induces polymerization of a MC within the lens. The polymerization of the MC, in turn, causes the change in optical properties.

In some examples, the optical element of the invention has dispersed within it a MC. The MC is capable of diffusion within the lens; can be readily polymerized by exposure to a suitable external stimulus; and is compatible with the materials used to make the first polymer matrix of the lens.

Figure 4:
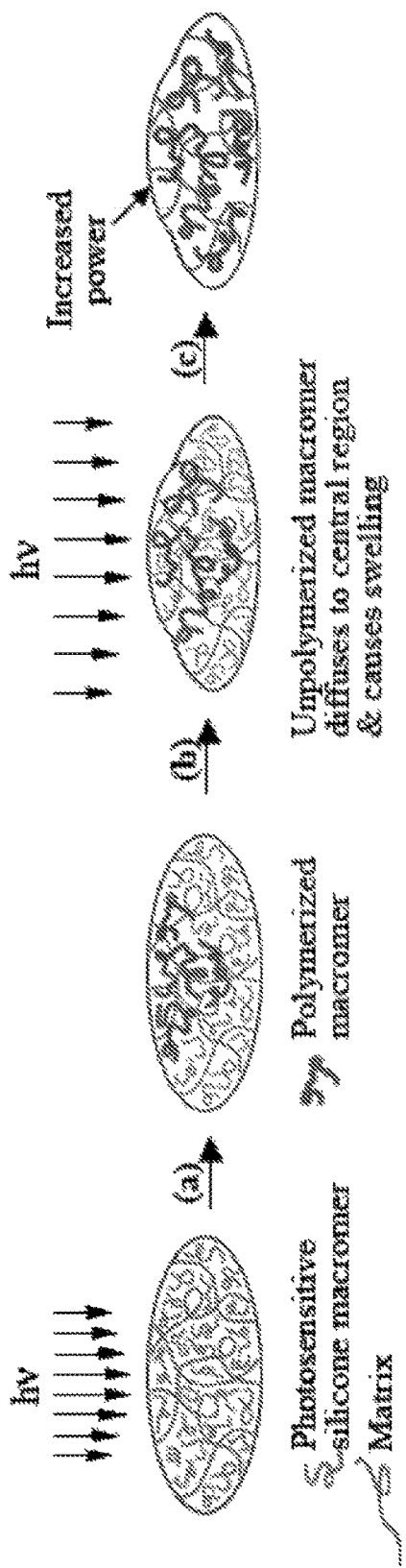
FIG. 4 shows a schematic of positive power adjustment mechanism; wherein (a) is a schematic representation of selective irradiation of the central zone of the lens in which the polymerization of the MC creates a difference in the chemical potential between the irradiated and non-irradiated regions, (b) to reestablish equilibrium, excess MC diffuses into the irradiated region causing, swelling, and (c) irradiation of the entire lens "locks" the remaining MC and the shape change.

The method for providing an aspheric lens begins with the formation of the first polymer matrix. After the first polymer matrix is formed, the second, polymer matrix is formed by exposing the first polymer matrix, which further comprises the MC, to an external stimulus. During this second polymerization, several changes occur within the optical element. The first change is the formation of a second polymer matrix comprising polymerized MC. The formation of the second polymer network can cause changes in the optical properties of the element, namely the refractive index. In addition, when the MC polymerizes, a difference, in the chemical potential between the polymerized and unpolymerized region is induced. This in turn causes the unpolymerized MC to diffuse within the element, which reestablishes thermodynamic equilibrium of the optical element If the optical element possesses sufficient elasticity, this migration of MC can cause swelling of the element in the area exposed to the stimulus. This, in turn, changes the shape of the element, causing changes in the optical properties. Whether the radius of curvature of the element and/or the refractive index of the element change depends upon (1) the nature of the optical element, (2) the MC incorporated into the element, (3) the duration that the element is exposed to the stimulus, and (4) the spatial intensity profile of the stimulus, A schematic depicting the process for increasing the power of the lens is displayed in FIG. 4.

The optical element is typically made of a first polymer matrix, illustrative, examples of a suitable first polymer matrix include: (1) polyacrylates such as polyalkyl acrylates and polyhydroxyalkyl acrylates; (2) polymethacrylates such as polymethyl methacrylate ("PMMA"), polyhydroxyethyl methacrylate ("PHEMA"), and polyhydroxypropyl methacrylate ("HPMA"); (3) polyvinyls such as polystyrene and polyvinylpyrrolidone ("PNVP"); (4) polysiloxanes such as polydimethylsiloxane; polyphosphazenes, and/or (5) copolymers thereof. U.S. Pat. No. 4,260,725 and patents and references cited therein (which are all incorporated herein by reference) provide more specific examples of suitable polymers that may be used to form the first polymer matrix.

In preferred embodiments, where flexibility is desired, the first polymer matrix generally possesses a relatively low glass transition temperature ("$T_g$") such that the resulting IOL tends to exhibit fluid-like and/or elastomeric behavior, and is typically formed by cross-linking one or more polymeric starting materials wherein each polymeric starting material includes at least one cross-linkable group. In the case of an intraocular lens, the $T_g$ should be less than 25° C. This allows the lens to be folded, facilitating implantation.

The crosslinking reaction of the polymeric material is accomplished via a hydrosilylation reaction. The general scheme for the hydrosilylation reaction is shown below.

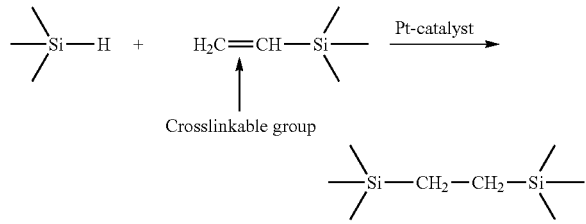

Crosslinkable group

During this crosslinking step, a high, molecular weight long vinyl-capped silicone polymer and multi-functional vinyl-capped silicone resin are crosslinked using multifunctional hydrosilane crosslinkers. This crosslinking step forms the first polymer matrix in the presence of MC and photoinitiator.

In some embodiments, the high molecular weight, long vinyl-capped silicone polymer has the following formula.

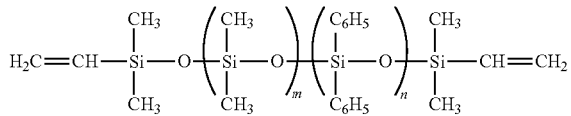

In some examples, m represents an integer having a value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges. In some examples, m represents an integer having an average value between 1 and 10,000; 1 and 9,500; 1 and 9,000; 1 and 8.500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges.

In some examples, n represents an integer having a value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges. In some examples, n represents an integer having an average value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges.

In some embodiments, multi-functional vinyl-capped silicone resin has the following formula.

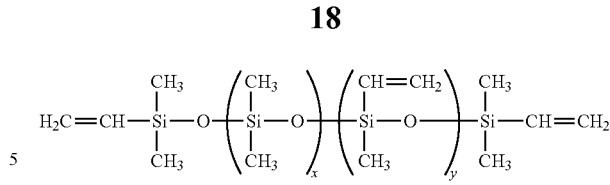

In some examples, x represents an integer having a value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges. In some examples, x represents an integer having an average value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges.

In some examples, y represents an integer having a value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges, in some examples, y represents an integer having an average value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges.

In some embodiments, multi-functional hydrosilane crosslinker has the following formula.

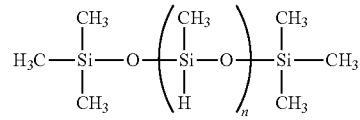

In some example n represents an integer having a value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5 000; 1 and 1,500; 1 and 4,000; 1 and 3,500; 1 and 3,000; 1 and 2,500; 1 and 2,000; 1 and 1,500; 1 and 1,000; 1 and 500 or any range found within any of the aforementioned ranges. In some examples, n represents an integer having an average value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges.

Illustrative examples of suitable cross-linkable groups include but are not limited to vinyl, hydride, acetoxy, alkoxy, amino, anhydride, aryloxy, carboxy, enoxy, epoxy, halide, isocyano, olefinic, and oxine. In more preferred embodiments, the polymeric starting material includes terminal monomers (also referred to as endcaps) that are either the same or different from the one or more monomers that comprise the polymeric starting material but include at least one cross-linkable group, in other words, the terminal monomers begin and end the polymeric starting material and include at least one cross-linkable group as part of its structure. Although it is not necessary for the practice of the present invention, the mechanism for cross-linking the polymeric starting material preferably is different than the mechanism for the stimulus-induced polymerization of the components that comprise the refraction modulating composition. For example, if the refraction modulating composition is polymerized by photoinduced polymerization, then it is preferred that the polymeric starting materials have cross-linkable groups that are polymerized by any mechanism other than photoinduced polymerization.

An especially preferred class of polymeric starting materials for the formation of the first polymer matrix is polysiloxanes (also known as "silicones") endcapped with a terminal monomer which includes a cross-linkable group selected from the group consisting of vinyl, acetoxy, amino, alkoxy, halide, hydroxy, and mercapto. Because silicone IOLs tend to be flexible and foldable, generally smaller incisions may be used during the IOL implantation procedure. An example of an especially preferred polymeric starting materials are vinyl endcapped dimethylsiloxane diphenylsiloxane copolymer, silicone resin, and silicone hydride crosslinker that are cross linked via an addition polymerization by platinum catalyst to form the silicone matrix (see the above reaction scheme). Other such examples may be found in U.S. Pat. Nos. 5,236,970; 5,376,694; 5,278,258; 5,444,106; and, others similar to the described formulations. U.S. Pat. Nos. 5,236,970; 5,376,694; 5,278,258; and 5,444,106 are incorporated herein by reference in their entirety.

The MC that is used in fabricating IOLs is as described above except that it has the additional requirement of biocompatibiliiy. The MC is capable of stimulus-induced polymerization and may be a single component or multiple components so long as: (1) it is compatible with the formation of the first polymer matrix; (2) it remains capable of stimulus-induced polymerization after the formation of the first polymer matrix; and (3) it is freely diffusible within the first polymer matrix. In general the same type of monomers that are used to form the first polymer matrix may be used as components of the refraction modulating composition. However, because of the requirement that the MC macromer must be diffusible within the first polymer matrix, the MC macromers generally tend to be smaller (i.e., have lower molecular weights) than the starting polymeric materials used to form the first polymer matrix. In addition to the one or more monomers, the MC may include other components such as initiators and sensitizers that facilitate the formation of the second polymer network.

In preferred embodiments, the stimulus-induced polymerization is photopolymerization. In other words, the one or more monomers or macromers that comprise the refraction modulating composition each preferably includes at least one group that is capable of photopolymerization. Illustrative examples of such photopolymerizable groups include but are not limited to acrylate, allyloxy, cinnamoyl, methacrylate, stibenyl, and vinyl. In more preferred embodiments, the refraction modulating composition includes a photoinitiator (any compound used to generate free radicals) either alone or in the presence of a sensitizer. Examples of suitable photoinitiators include acetophenones (e.g., substituted haloacetophenones, and diethoxyacetophenone); 2,4-dichloromethyl-1,3,5-trazines; benzoin methyl ether; and o-benzoyl oximino ketone. Examples of suitable sensitizers include p-(dialkyiamino)aryl aldehyde; N-alkylindolylidene; and bis[p-(dialkylamino)benzylidene] ketone.

Because of the preference for flexible and foldable IOLs, an especially preferred class of MC monomers is polysiloxanes endcapped with a terminal, siloxane moiety that includes a photopolymerizable group. Non-limiting examples of a suitable photopolymerizable group include, but are not limited to acrylate, allyloxy, cinnamoyl, methacrylate, stibenyl, and vinyl. An illustrative representation of such a monomer is:

wherein Y is a siloxane which may be a monomer, a homopolymer or a copolymer formed from any number of siloxane units, and X and $X^1$ may be the same or different and are each independently a terminal siloxane moiety that includes a photopolymerizable group. Non-limiting examples of a suitable photopolymerizable group include., but are not limited to acrylate, allyloxy, cinnamoyl, methacrylate, stibenyl, and vinyl. An illustrative example of Y includes:

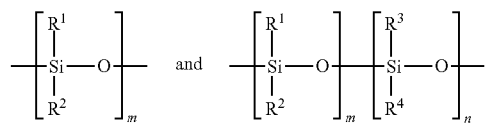

wherein m and n are independently each an integer; and, $R^1$, $R^2$, $R^3$, and $R^4$ are independently each hydrogen, alkyl (substituted, primary, secondary, tertiary, cycloalkyl), aryl, or heteroaryl. In preferred embodiments, $R^1$, $R^2$, $R^3$, and $R^4$ are independently $C_1$-$C_{10}$ alkyl or phenyl. Because MC monomers with a relatively high aryl content have been found to produce larger changes in the refractive index of the inventive lens, it is generally preferred that at least one of $R^1$, $R^2$, $R^3$, and $R^4$ is an aryl, particularly phenyl. In more preferred embodiments, $R^1$, $R^2$, and $R^3$ are the same and are methyl, ethyl or propyl with the proviso that $R^4$ is phenyl.

In some examples, m represents an integer having a value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges. In some examples, m represents an integer having an average value between 1 and 10,000; 1 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges.

In some examples, n represents an integer having a value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000: 1 and 2,500; 1 and 2,000; 1 and 1,500; 1 and 1,000; 1 and 500 or any range found within any of the aforementioned ranges. In some examples, n represents an integer having an average value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; J and 1,000; 1 and 500 or any range found within any of the aforementioned ranges.

illustrative examples of X and $X^1$ (or $X^1$ and X depending on how the MC polymer is depicted) are:

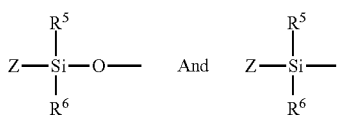

respectively wherein; $R^5$ and $R^6$ are independently each hydrogen, alkyl, aryl, or heteroaryl; and Z is a photopolymerizable group.

In preferred embodiments $R^5$ and $R^6$ are independently each $C_1$-$C_{10}$ alkyl or phenyl and Z is a photopolymerizable group that includes a moiety selected from the group consisting of acrylate, allyloxy, cinnamoyl, methacrylate, stibenyl, and vinyl. In more preferred embodiments, $R^5$ and $R^6$ are methyl, ethyl, or propyl and Z is a photopolymerizable group that includes an acrylate or methacrylate moiety.

In some embodiments, a MC macromer has the following formula:

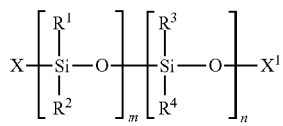

wherein X and $X^1$ are the same as defined above, and wherein $R^1$, $R^2$, $R^3$, and $R^4$ are the same as defined above. In some examples, m represents an integer having a value between 1 and 10,000; 1 mid 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges. In some examples, m represents an integer having an average value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges.

In some examples, n represents an integer having a value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 5 and 3,000; 1 and 2,500; 1 and 2,000; 1 and 1,500; 1 and 1,000; 1 and 500 or any range found within any of the aforementioned ranges. In some examples, n represents an integer having an average value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges.

In general, a suitable modifying composition consists of a lower molecular weight polydimethyl-siloxane macromer containing polymerizable methaerylate functional end groups and a bezoin photoinitiator. In some embodiments, a suitable modifying composition has the following formula.

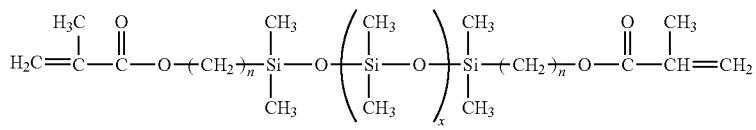

The above structure is a polydimethyl siloxane end-capped with photopolymerizable methacrylate functional groups. In some examples, x represents an integer having a value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges. In some examples, x represents an integer having an average value between 1 and 10,000; 1 and 9,500; 1 and 9,000; 1 and 8,500; 1 and. 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges.

In some examples, n represents an integer having a value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges. In some examples, n represents an integer having an average value between 1 and 10,000: 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges.

In some embodiments, a suitable modifying composition has the following formula.

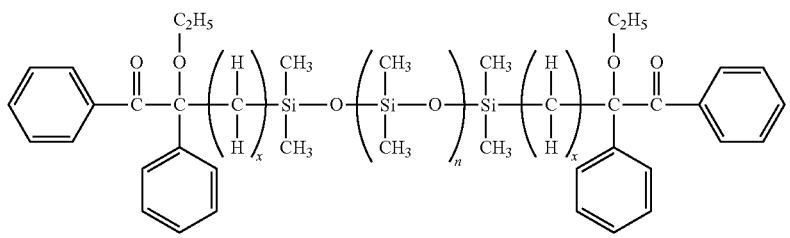

The above modifying composition has a structure comprising a polydimethyl siloxane end-capped with benzoin photoinitiator. In some examples, x represents an integer having a value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges. In some examples, x represents an integer having an average value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges.

In some examples, n represents an integer having a value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges. In some examples, n represents an integer having an average value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges.

Additional illustrative examples of such MC monomers include dimethylsiloxane-diphenylsiloxane copolymer end-capped with a vinyl dimethylsilane group (see below);

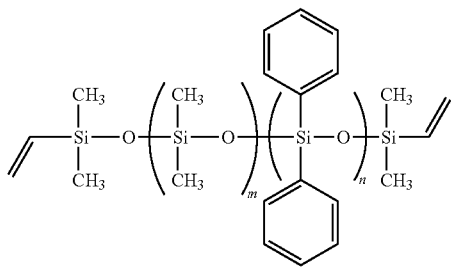

In some examples, m represents an integer having a value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges. In some examples, m represents an integer basing an average value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges.

In some examples, n represents an integer having a value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges. In some examples, n represents an integer having an average value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges.

Another illustrative examples of such MC monomers includes dimethylsiloxane-methylphenylsiloxane copolymer endcapped with a methacryloxypropyl dimethylsilane group (see below);

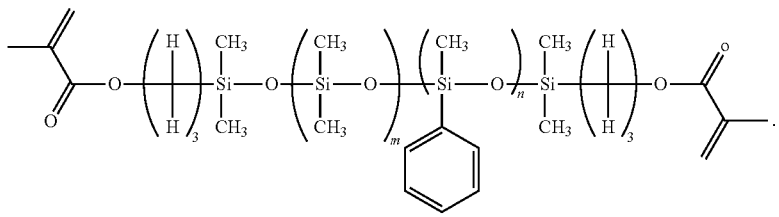

In some examples, m represents an integer having a value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges. In some examples, m represents an integer having an average value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges.

In some examples, n represents an integer having a value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges. In some examples, n represents an integer having an average value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges.

A preferred modifying composition is the dimethylsiloxane macromer endcapped with a methacryloxypropyldimethylsilane group (see below).

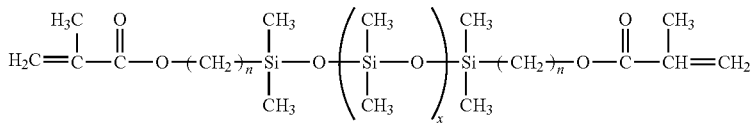

In some examples, x represents an integer having a value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned, ranges. In some examples, x represents an integer having an average value between 1 and 10,000; 1 and 9,500; 1 and 9,000; 1 and 8,500; 1 and 8,000; 1 and 7,500; 1 and 7,000; 1 and 6,500; 1 and 6,000: 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges.

In some examples, n represents an integer having a value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges. In some examples, n represents an integer having an average value between 1 and 10.000: 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges.

Although any suitable method may be used, a ring-opening reaction of one or more cyclic siloxanes in the presence of triflic acid has been found to be a particularly efficient method of making a class of MC monomers. Briefly, the method, comprises contacting a cyclic siloxane with a compound of the formula:

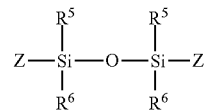

in the presence of triflic acid wherein $R^5$ and $R^6$ are independently each hydrogen, alkyl, aryl, or heteroaryl; and Z is a photopolymerizable group. The cyclic siloxane may be a cyclic siloxane monomer, homopolymer, or copolymer. Alternatively, more than one cyclic siloxane may be used. For example, a cyclic dimethylsiloxane tetrameter and a cyclic methyl-phenylsiloxane trimer are contacted with bis-methacryloxypropyitetramethyldisiloxane in the presence of triflic acid to form a dimethyl-siloxane methyl-phenylsiloxane copolymer that is endcapped with a methacryloxylpropyl-dimethylsilane group, an especially preferred MC monomer, such as the MC monomer shown below.

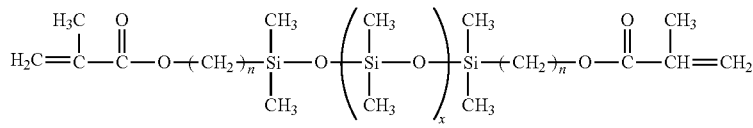

In some examples, x represents an integer having a value between 1 and 10,000; 1 and 9,500; 1 and 9,000; 1 and 8,500; 1 and 8,000; 1 and 7,500; 1 and 7,000; 1 and 6,500; 5 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges. In some examples, x represents an integer having an average value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges.

In some examples, n represents an integer having a value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges. In some examples, n represents an integer having an average value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges.

In addition to the silicone-based MCs described above, acrylate-based MC can also be used in the practice of the invention. The acrylate-based macromers of the invention have the general structure wherein X and X/u$^1$ may be the same or different and/or are each independently a terminal siloxane moiety that includes a photopolymerizable group. Non-limiting examples of a suitable photopolymerizable group include, but are not limited to acrylate, allyloxy, cinnamoyl, methacrylate, stibenyl, and vinyl

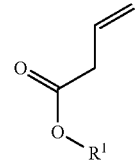

wherein $R^1$ is selected from the group comprising alkyls, halogenated alkyls, aryls and halogenated aryls and X and $X^1$ are groups containing photopolymerizable moieties and m and n are integers. In some examples, m represents an integer having a value between 1 and 10,000; 1 and 9,500; 1 and 9,000; 1 and 8,500; 1 and 8,000; 1 and 7,500; 1 and 7,000; 1 and 6,500; 1 and 6,100; 1 and 5,500; 1 and 5,000; 1 and 4,500; and 4,000; 1 and 3,500; 1 and 3,000; 1 and 2,500; 1 and 2,000; 1 and 1,500; 1 and 1,000; 1 and 500 or any range found within any of the aforementioned ranges. In some examples, m represents an integer having an average value between 1 and 10,000; and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges.

In some examples, n represents an integer having a value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges. In some examples, n represents an integer having an average value, between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges.

In one embodiment the acrylate based MC macromer has the formula:

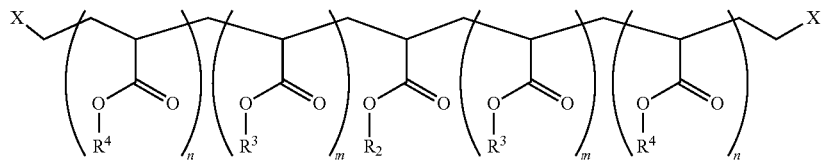

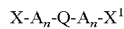

or

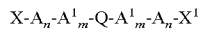

wherein Q is an acrylate moiety capable of acting as an initiator for Atom Transfer Radical Polymerization ("ATRP"), A and $A^1$ have the general structure:

wherein $R^2$ is alkyl or halogenated alkyl; $R^3$ is alkyl, halogenated alkyl, aryl or halogenated aryls; $R^4$ is alkyl, halogenated alkyl, aryl or halogenated aryl; and, with the proviso that $R^3$ and $R^4$ are different In some embodiments, the value of n is between 1 and 200; 1 and 190; 1 and 180; 1 and 170; 1 and 160; 1 and 150; 1 and 140; 1 and 130; 1 and 120; 1 and 110; 1 and 100; 1 and 90; 1 and 80; 1 and 70; 1 and 60; 1 and 50; 1 and 40; 1 and 30; 1 and 20; 1 and 10; or any range in between. For example, when the value of n is between 1 and 200, this also contemplates a value of n between 17 and 24. In some embodiments the value of m is between 1 and 200; 1 and 190; 1 and 180; 1 and 170; 1 and 160; 1 and 150; 1 and 140; 1 and 130; 1 and 120; 1 and 110; 1 and 100; 1 and 90; 1 and 80; 1 and 70; 1 and 60; 1 and 50; 1 and 40; 1 and 30; 1 and 20; 1 and 10; or any range in between. For example, when the value of m is between 1 and 200, this also contemplates a value of m between 17 and 24.

After the optical element is formed, it is then positioned in the area where the optical properties ate to be modified. For an intraocular lens, this means implantation into the eye using known procedures. Once the element is in place and is allowed to adjust to its environment, it is then possible to modify the optical properties of the element through exposure to an external stimulus.

The nature of the external stimulus can vary but it must be capable of reducing polymerization of the MC without adversely affecting the properties of the optical element. Typical external stimuli that can be used in practice of the invention include heat and light, with light preferred. In the case of intraocular lenses, ultraviolet or infrared radiation is preferred with ultraviolet light most preferred.

When the element is exposed to the external stimulus, the MC polymerization forms a second polymer matrix, interspersed within the first polymer matrix. When the polymerization is localized or when only a portion of the MC is polymerized, there is a difference in the chemical potential between the reacted and unreacted regions of the lens. The MC then migrates within the element to reestablish the thermodynamic equilibrium within the optical element.

The formation of the second polymer matrix and the re-distribution of the MC can each affect the optical properties of the element. For example, the formation of the second polymer matrix can cause changes in the refractive index of the element. The migration of the modifying compound can alter the overall shape of the element, further affecting the optical properties by changing the radii of curvatures of the optical element.

Figure 5:
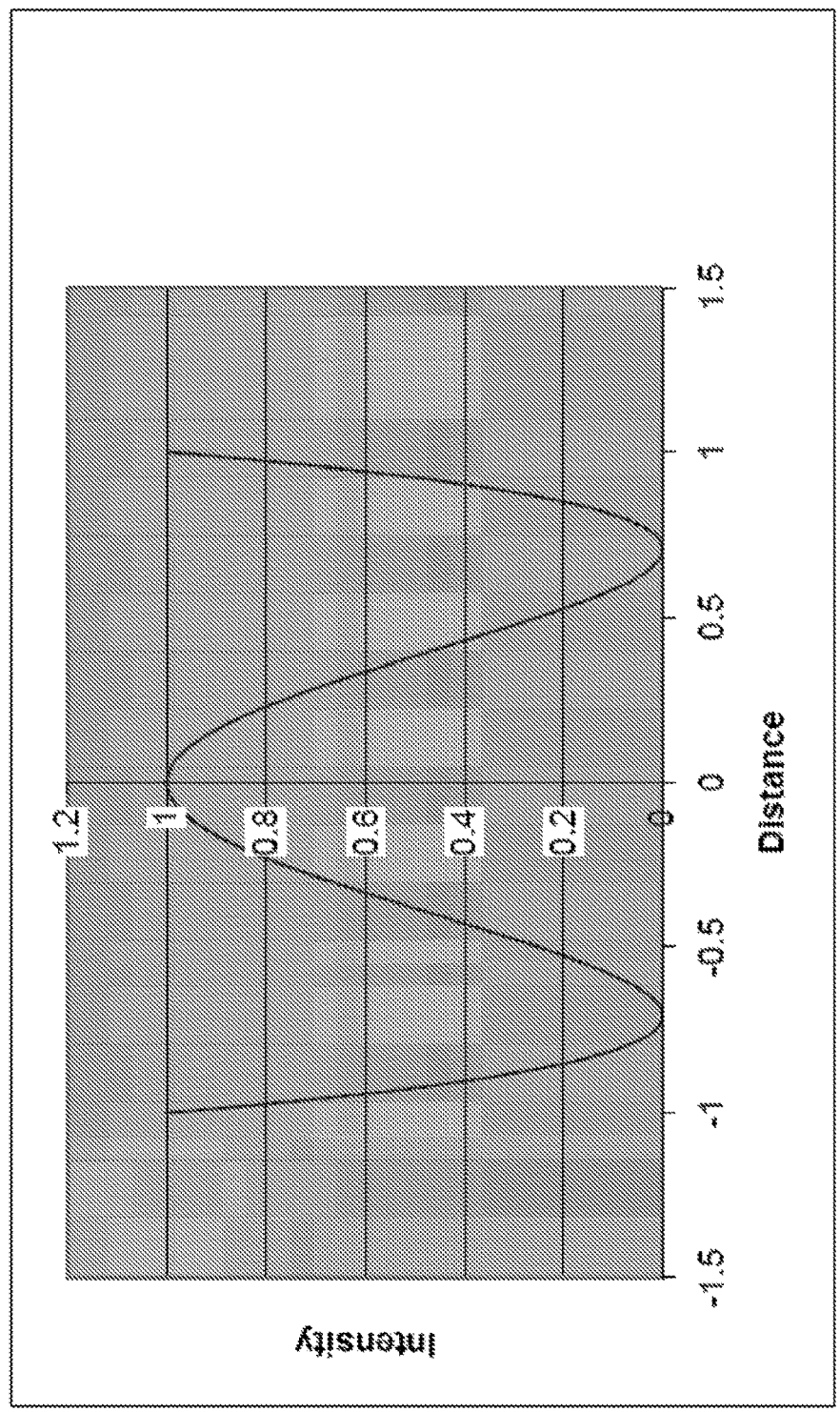
FIG. 5 shows a plot of the aspheric function described in Equation 1.

It is possible to expose the optical element to a spatially defined irradiance profile to create a lens with different optical properties. In one embodiment, it is possible to create an intraocular lens that can be converted into an aspheric lens after implantation. This is accomplished by exposing the lens to a mathematically defined spatial irradiance profile. An example of the type of profiles that can be used to induce asphericity in the lens are of the form $$\text{Asph}(\rho)=A\rho^4-B\rho^2+1 \quad \text{(Equation 1)}$$

where A and B are coefficients and $\rho$ is a radial coordinate. A normalized plot of this function, where A=B=4, is displayed in FIG. 5.

Figure 6:
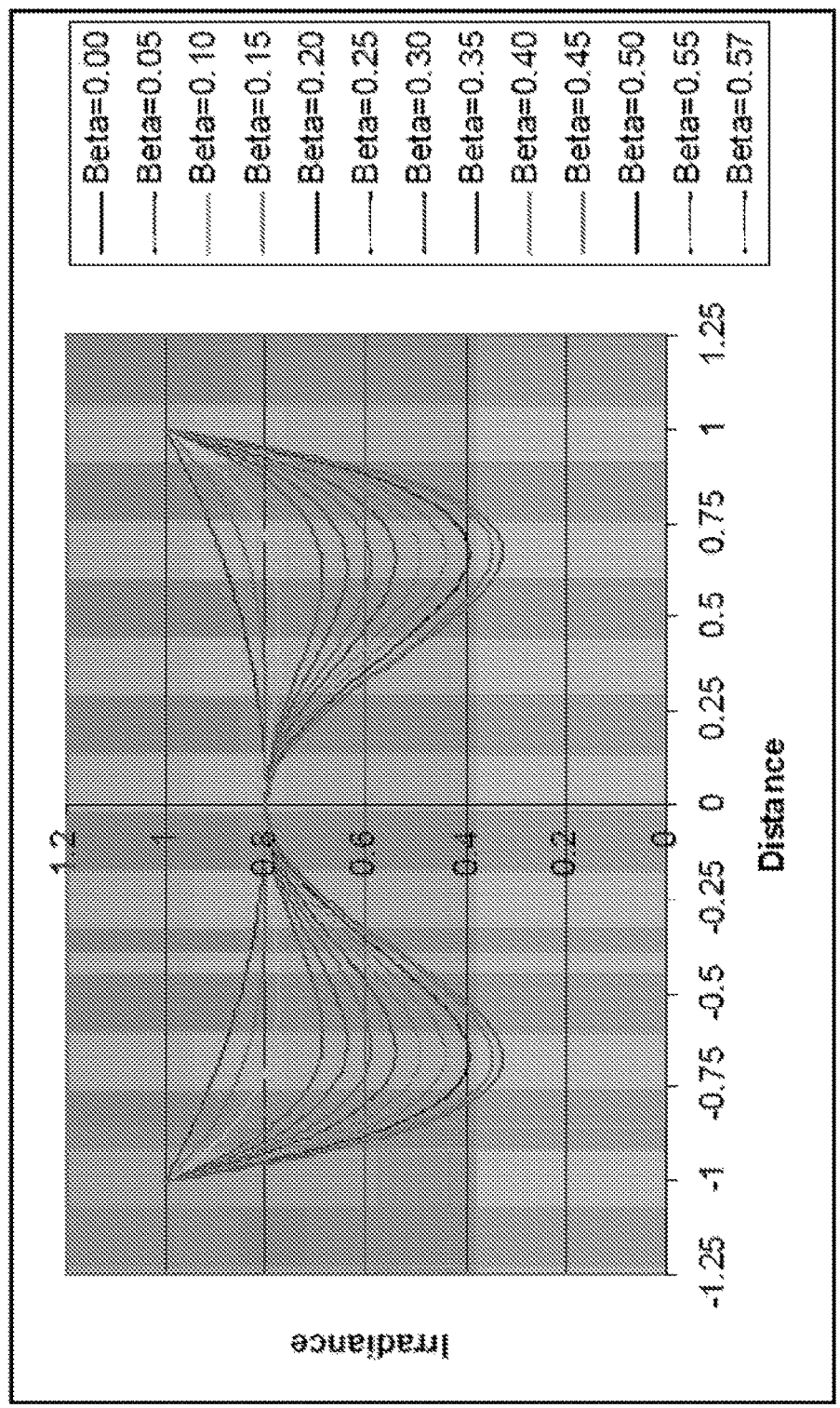
FIG. 6 shows cross-sectional plots of Equation 2 generated by combining a power neutral profile with weighted amounts ($\beta$=0 to 0.57) of the aspheric profile.

Another approach is to linearly combine weighted amounts of the profile (Asph) displayed in equation 1 with spatial irradiance profiles that are currently used to correct for spherical refractive errors and spherocylindrical refractive errors as well as with Power Neutral Profiles, i.e., profiles that neither add or subtract refractive power from the LAL. This approach has the dual benefits of correcting the lower aberrations, e.g. sphere and cylinder, along with imparting the requisite amount of induced asphericity to provide increased depth of focus. This can be described mathematically as follows:

$$\text{Profile}(\rho)=\text{SCN}(\rho)+\beta\text{Asph}(\rho) \quad \text{(Equation 2)}$$

where $\text{SCN}(\rho)$ refers to either a spherical, spherocylindrical or power neutral spatial irradiance profile, $\text{Asph}(\rho)$ is the same as in equation 1, and $\beta$ is a weighting factor that can range from 0 to 1. As an example of this approach, consider the cross-sectional profiles shown in FIG. 6. These plots were generated by combining weighted amounts of the profile represented by equation 1 with a power neutral profile.

By way of a reaction sequence, the following example shows how the formation of the second polymer matrix and the re-distribution of the MC is accomplished. In the example provided below, the MC having the formula:

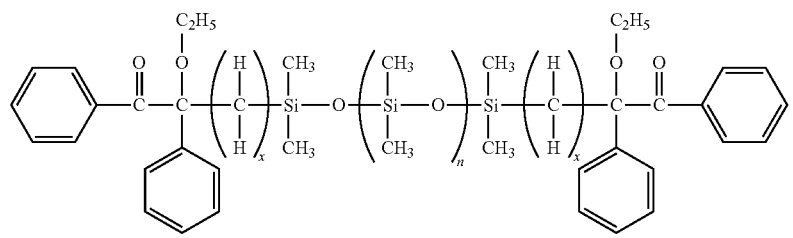

is exposed to UV light, thereby creating a radical species. This process is represented schematically in the reaction scheme below.

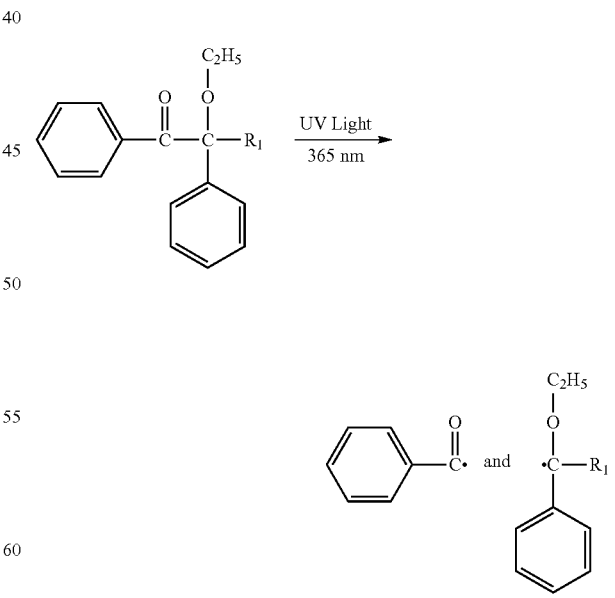

After exposing the MC to UV light, the resulting radical, species are free to react with the first polymer matrix. In the example, below the first polymer matrix was formed using a polymer having the following structure:

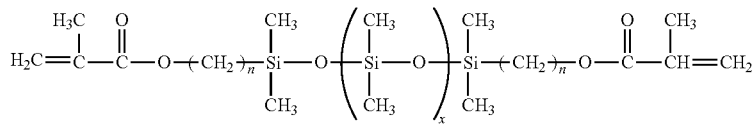

The radical species generated by exposing the MC to UV light then reacts with the first polymer matrix according to the reaction scheme below:

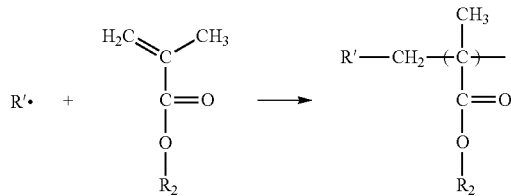

where,

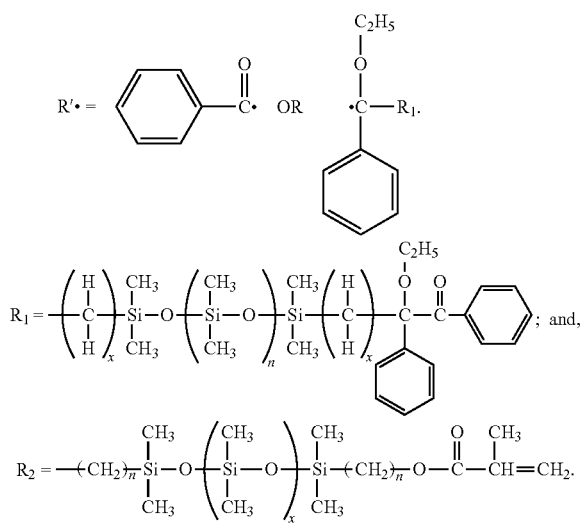

The reaction scheme for photopolymerization of photoreactive MC in the presence of the first polymer lens matrix is the same for the adjustment and lock-in procedures. The difference between the adjustment procedure and lock-in procedure is the spatial irradiance profiles applied to each procedure.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Figure 7:
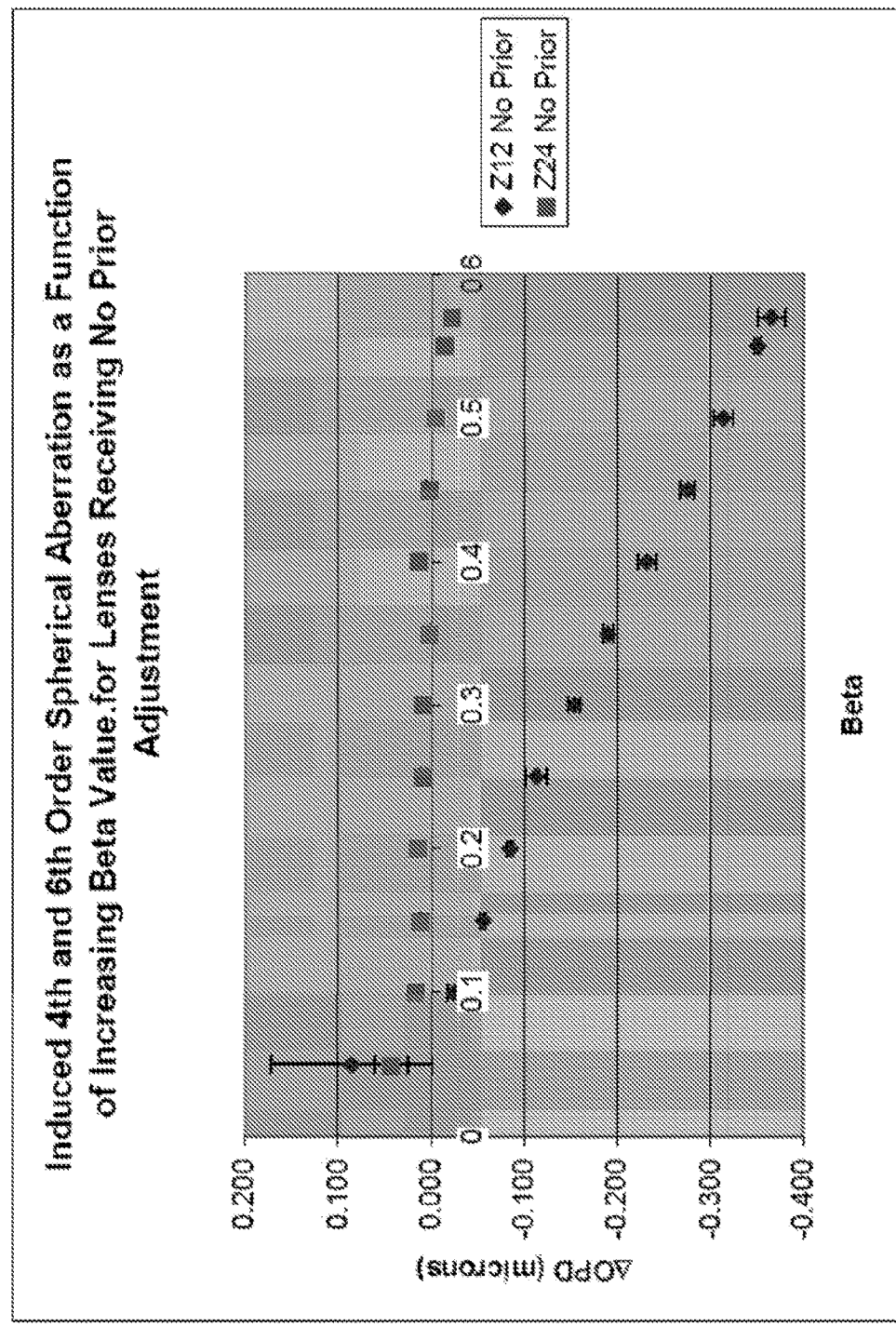
FIG. 7 shows a plot of induced $4^{th}$ and $6^{th}$ order spherical aberration as a function of increasing $\beta$ value. The measurement aperture was 4 mm and none of these LALs received any type of prior adjustment.

A series of light adjustable lenses containing a silicone-based MC were prepared using standard molding techniques known to those skilled in the art. The lens had a first polymer matrix prepared from a silicone hydride crosslinked vinyl endcapped diphenylsiloxane dimethylsiloxane. The first polymer matrix comprised about 70 weight % of the lens. The lens also comprised about 30 weight % of a MC (methacrylate endcapped polydimethylsiloxane), 1 weight % (based on MC) of a photoinitiator (benzoin-tetrasiloxane-benzoin), and 0.04 weight % (based on MC) UV absorber. The lenses had an initial nominal power of +20.0 diopters. Twelve groups, of four LALs each, were exposed to a spatial irradiance profile defined by Equation 2 with beta values ranging from 0.05 to 0.57. Table 1 summarizes the specific spatial irradiance profile, average irradiance, and time applied to each of the LAL groups. At 48 hours post irradiation, the wavefronts of each of the lenses was measured. The measured $4^{th}$ (Z12) and $6^{th}$ (Z24) order spherical aberration values for each of the 12 irradiation groups were averaged together and plotted as a function of increasing β value as show in FIG. 7.

TABLE 1

Summary of treatment conditions and induced spherical aberration for those lenses that did not receive a prior adjustment. The measurement aperture was 4 mm for all spherical aberration measurements.

| Lens ID | Profile | Duration (sec) | Applied Power (mW) | Bm Size (mm) | Δ 4th Order SA Δ Z12 (μm) | Δ 6th Order SA Δ Z24 (μm) |
|---|---|---|---|---|---|---|
| 6699 | In-vitro PN Profile + Beta = 0.05 | 90 | 4.130 | 5.30 | 0.194 | 0.016 |
| 6701 | In-vitro PN Profile + Beta = 0.05 | 90 | 4.130 | 5.30 | 0.115 | 0.050 |
| 6706 | In-vitro PN Profile + Beta = 0.05 | 90 | 4.130 | 5.30 | 0.003 | 0.054 |
| 6708 | In-vitro PN Profile + Beta = 0.05 | 90 | 4.130 | 5.30 | 0.029 | 0.053 |
| Average | | | | | 0.085 | 0.043 |
| St. Dev | | | | | 0.087 | 0.018 |

TABLE 1-continued

Summary of treatment conditions and induced spherical aberration for those lenses that did not receive a prior adjustment. The measurement aperture was 4 mm for all spherical aberration measurements.

| Lens ID | Profile | Duration (sec) | Applied Power (mW) | Bm Size (mm) | Δ4th Order SA Δ Z12 (μm) | Δ 6th Order SA Δ Z24 (μm) |
|---|---|---|---|---|---|---|
| 189-26 | In-vitro PN Profile + Beta = 0.10 | 90 | 3.820 | 5.30 | −0.019 | 0.017 |
| 189-29 | In-vitro PN Profile + Beta = 0.10 | 90 | 3.820 | 5.30 | −0.024 | 0.017 |
| 189-31 | In-vitro PN Profile + Beta = 0.10 | 90 | 3.820 | 5.30 | −0.020 | 0.016 |
| 189-33 | In-vitro PN Profile + Beta = 0.10 | 90 | 3.820 | 5.30 | −0.036 | 0.013 |
| Average | | | | | −0.025 | 0.016 |
| St. Dev | | | | | 0.008 | 0.002 |
| 189-27 | In-vitro PN Profile + Beta = 0.15 | 90 | 3.670 | 5.30 | −0.056 | 0.013 |
| 189-30 | In-vitro PN Profile + Beta = 0.15 | 90 | 3.670 | 5.30 | −0.055 | 0.013 |
| 189-32 | In-vitro PN Profile + Beta = 0.15 | 90 | 3.670 | 5.30 | −0.054 | 0.012 |
| 189-34 | In-vitro PN Profile + Beta = 0.15 | 90 | 3.670 | 5.30 | −0.060 | 0.010 |
| Average | | | | | −0.056 | 0.012 |
| St. Dev | | | | | 0.003 | 0.001 |
| 189-35 | In-vitro PN Profile + Beta = 0.20 | 90 | 3.510 | 5.30 | −0.088 | 0.018 |
| 189-38 | In-vitro PN Profile + Beta = 0.20 | 90 | 3.510 | 5.30 | −0.088 | 0.013 |
| 189-40 | In-vitro PN Profile + Beta = 0.20 | 90 | 3.510 | 5.30 | −0.083 | 0.018 |
| 189-44 | In-vitro PN Profile + Beta = 0.20 | 90 | 3.510 | 5.30 | −0.081 | 0.013 |
| Average | | | | | −0.085 | 0.015 |
| St. Dev | | | | | 0.003 | 0.003 |
| 189-37 | In-vitro PN Profile + Beta = 0.25 | 90 | 3.360 | 5.30 | −0.107 | 0.013 |
| 189-39 | In-vitro PN Profile + Beta = 0.25 | 90 | 3.360 | 5.30 | −0.111 | 0.006 |
| 189-41 | In-vitro PN Profile + Beta = 0.25 | 90 | 3.360 | 5.30 | −0.106 | 0.009 |
| 189-45 | In-vitro PN Profile + Beta = 0.25 | 90 | 3.360 | 5.30 | −0.130 | 0.006 |
| Average | | | | | −0.113 | 0.009 |
| St. Dev | | | | | 0.011 | 0.003 |
| 185-3-2 | In-vitro PN Profile + Beta = 0.30 | 90 | 3.210 | 5.30 | −0.151 | 0.010 |
| 185-3-15 | In-vitro PN Profile + Beta = 0.30 | 90 | 3.210 | 5.30 | −0.156 | 0.008 |
| 188-2-18 | In-vitro PN Profile + Beta = 0.30 | 90 | 3.210 | 5.30 | −0.163 | 0.012 |
| 189-47 | In-vitro PN Profile + Beta = 0.30 | 90 | 3.210 | 5.30 | −0.148 | 0.007 |
| Average | | | | | −0.155 | 0.009 |
| St. Dev | | | | | 0.007 | 0.002 |
| 185-3-11 | In-vitro PN Profile + Beta = 0.35 | 90 | 3.060 | 5.30 | −0.193 | 0.005 |
| 188-2-16 | In-vitro PN Profile + Beta = 0.35 | 90 | 3.060 | 5.30 | −0.194 | 0.003 |
| 189-46 | In-vitro PN Profile + Beta = 0.35 | 90 | 3.060 | 5.30 | −0.192 | 0.002 |
| 189-48 | In-vitro PN Profile + Beta = 0.35 | 90 | 3.060 | 5.30 | −0.182 | 0.002 |
| Average | | | | | −0.190 | 0.003 |
| St. Dev | | | | | 0.006 | 0.002 |
| 6700 | In-vitro PN Profile + Beta = 0.40 | 90 | 2.900 | 5.30 | −0.240 | 0.013 |
| 6704 | In-vitro PN Profile + Beta = 0.40 | 90 | 2.900 | 5.30 | −0.241 | 0.011 |
| 6707 | In-vitro PN Profile + Beta = 0.40 | 90 | 2.900 | 5.30 | −0.222 | 0.011 |
| 6709 | In-vitro PN Profile + Beta = 0.40 | 90 | 2.900 | 5.30 | −0.224 | 0.017 |
| Average | | | | | −0.232 | 0.013 |
| St. Dev | | | | | 0.010 | 0.003 |
| 6710 | In-vitro PN Profile + Beta = 0.45 | 90 | 2.750 | 5.30 | −0.277 | 0.004 |

TABLE 1-continued

Summary of treatment conditions and induced spherical aberration for those lenses that did not receive a prior adjustment. The measurement aperture was 4 mm for all spherical aberration measurements.

| Lens ID | Profile | Duration (sec) | Applied Power (mW) | Bm Size (mm) | Δ4th Order SA Δ Z12 (μm) | Δ 6th Order SA Δ Z24 (μm) |
|---|---|---|---|---|---|---|
| 6712 | In-vitro PN Profile + Beta = 0.45 | 90 | 2.750 | 5.30 | −0.284 | 0.003 |
| 6715 | In-vitro PN Profile + Beta = 0.45 | 90 | 2.750 | 5.30 | −0.274 | 0.006 |
| 6717 | In-vitro PN Profile + Beta = 0.45 | 90 | 2.750 | 5.30 | −0.266 | −0.002 |
| Average | | | | | −0.275 | 0.003 |
| St. Dev | | | | | 0.007 | 0.003 |
| 6713 | In-vitro PN Profile + Beta = 0.50 | 90 | 2.600 | 5.30 | −0.303 | 0.001 |
| 6716 | In-vitro PN Profile + Beta = 0.50 | 90 | 2.600 | 5.30 | −0.322 | −0.002 |
| 6718 | In-vitro PN Profile + Beta = 0.50 | 90 | 2.600 | 5.30 | −0.318 | −0.009 |
| Average | | | | | −0.314 | −0.003 |
| St. Dev | | | | | 0.010 | 0.005 |
| 6719 | In-vitro PN Profile + Beta = 0.55 | 90 | 2.440 | 5.30 | −0.356 | −0.009 |
| 6723 | In-vitro PN Profile + Beta = 0.55 | 90 | 2.440 | 5.30 | −0.347 | −0.016 |
| 6727 | In-vitro PN Profile + Beta = 0.55 | 90 | 2.440 | 5.30 | −0.350 | −0.011 |
| 6729 | In-vitro PN Profile + Beta = 0.55 | 90 | 2.440 | 5.30 | −0.350 | −0.021 |
| Average | | | | | −0.351 | −0.014 |
| St. Dev | | | | | 0.004 | 0.006 |
| 6721 | In-vitro PN Profile + Beta = 0.57 | 90 | 2.380 | 5.30 | −0.368 | −0.015 |
| 6725 | In-vitro PN Profile + Beta = 0.57 | 90 | 2.380 | 5.30 | −0.350 | −0.026 |
| 6728 | In-vitro PN Profile + Beta = 0.57 | 90 | 2.380 | 5.30 | −0.359 | −0.019 |
| 6730 | In-vitro PN Profile + Beta = 0.57 | 90 | 2.380 | 5.30 | −0.385 | −0.030 |
| Average | | | | | −0.366 | −0.022 |
| St Dev | | | | | 0.015 | 0.007 |

Inspection of the plot indicates several interesting features. The first is the nearly linearly increase in induced $4^{th}$ order spherical aberration as a function of increasing β value. The second feature is the nearly complete absence of any $6^{th}$ order spherical aberration induction, indicating that the induced spherical aberration is essentially pure $4^{th}$ order spherical aberration. This is important because it has been shown that the presence of $6^{th}$ order spherical aberration will have the affect of nulling out any induced depth of focus produced by the induction of negative $4^{th}$ order spherical aberration. (Thibos et al., 2004) The third feature to note is the small standard deviation in the average, induced $4^{th}$ order spherical aberration for a specific β value. This fact indicates that it is possible to adjust the amount of asphericity in the LAL by targeted, discrete values, which will allow true customization of patients' depth of focus. And finally, as written above, the targeted amount of total ocular $4^{th}$ order spherical aberration for optimizing visual acuity between 40 cm and distance emmetropia is −0.125 μm. Inspection, of the data in Table 2 and FIG. 7 and assuming an average starting ocular spherical aberration at a 4 mm aperture of +0.10 μm, indicates that the profile with a beta value of 0.40 would be ideal for inducing the requisite amount of negative asphericity.

The above example involved irradiating LALs that had not received a prior adjustment. However, there will be instances where it is necessary to first adjust the spherical and/or spherocylindrical power of the LAL before the aspheric adjustment. The LAL is a closed thermodynamic system, i.e. we can't add or remove particles, MC, from the lens. As a consequence, each subsequent refractive adjustment consumes MC leaving less for subsequent adjustments. In addition, upon polymerization of MC during adjustment, the polymerized MC forms an interpenetrating matrix with the host matrix polymer. This action has the effect of increasing the stiffness of the lens. Because the refractive change, i.e. spherical, spherocylindrical, aspheric, etc., of the LAL is accomplished by a shape change, the amount of induced asphericity after an initial adjustment should be reduced for same treatment conditions as with the no prior adjustment cases summarized in FIG. 7.

Figure 8:
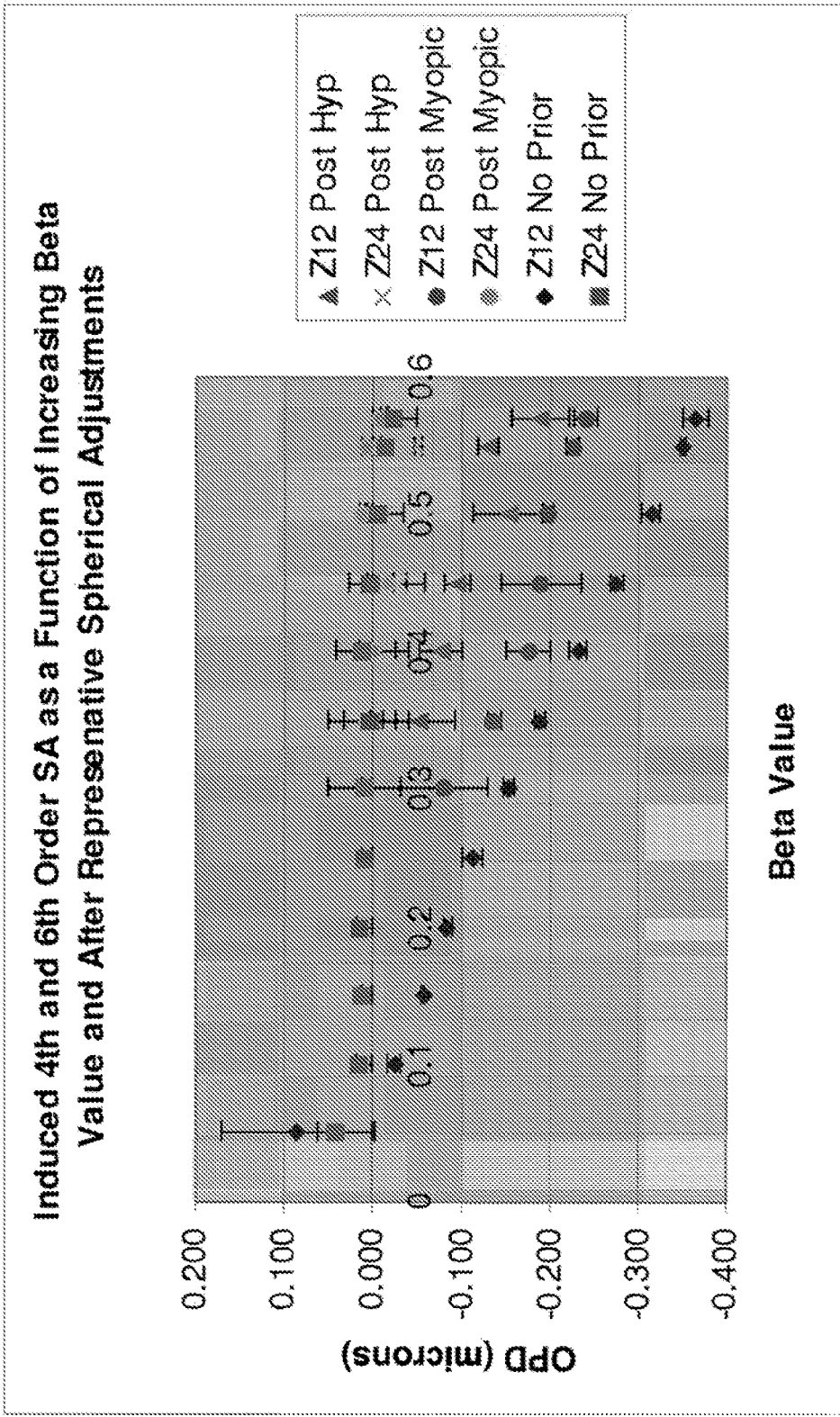
FIG. 8 shows a plot of induced $4^{th}$ and $6^{th}$ order spherical aberration as a function of increasing $\beta$ value for LALs receiving a hyperopic, myopic, and no prior adjustment. The measurement aperture for both the $4^{th}$ and $6^{th}$ order spherical aberration was 4 mm.

To investigate this, a series of LALs were initially given either a myopic or hyperopic primary adjustment followed by an aspheric treatment 48 hours post the initial, primary adjustment. FIG. 8 displays both the $4^{th}$ and $6^{th}$ order spherical aberration values for LALs that received either an initial hyperopic or myopic adjustment followed by an aspheric treatment with beta values ranging between 0.30 and 0.57. For comparison, the LALs that received the aspheric treatment as a primary adjustment are also plotted on the same graph.

Inspection and comparison of the data for the different treatment conditions indicate several interesting trends. The first overall theme is that, as expected, increasing the beta value, which effectively increases the amount of aspheric character of the treatment beam, has the effect of increasing the amount, of induced $4^{th}$ order asphericity in the LAL. This is true whether the LAL initially received a primary adjustment or if the LAL has received no prior adjustment. The second thing to note is that for a given beta, mediated aspheric profile, the type of refractive adjustment preceding the aspheric treatment directly impacts how much $4^{th}$ order asphericity is induced in the lens. For example, consider the three different sets of LALs that were adjusted with the $\beta=0.57$ aspheric profile after a hyperopic adjustment, a myopic adjustment, and no adjustment. Inspection of the graph indicates that those lenses receiving no prior adjustment displayed the largest amount of induced $4^{th}$ order spherical aberration, followed by the LALs that initially received a myopic adjustment, with the LALs after a hyperopic adjustment showing the smallest amount of induced asphericity. The reasons for this general trend are twofold. The first, which was discussed above, is due to the simple fact that the LALs that received no prior adjustment obviously have more starting MC and the LAL matrix is not as stiff as compared to the other two sets of LALs and thus, for the same given, aspheric dose, should show more $4^{th}$ order asphericity induction. The reasons why the LALs receiving an initial myopic adjustment display greater amounts of induced $4^{th}$ order spherical aberration as compared to those LALs receiving a hyperopic adjustment as their primary adjustment, even though the magnitude of the refractive change (−1.0 D vs +1.0 D) is the same, can be explained by the fact that the total energy underneath the spatial irradiance profile for the given myopic adjustment is less than that as compared to the hyperopic adjustment profile. Because of this fact, more macromer will be consumed during the initial hyperopic adjustment and a stronger, interpenetrating network will be formed, thus preventing more aspheric induction. Another important aspect of the data to note, is that regardless of prior adjustment, the application of the aspheric treatment does not induce any $6^{th}$ order spherical aberration.

Example 2

Figure 9:
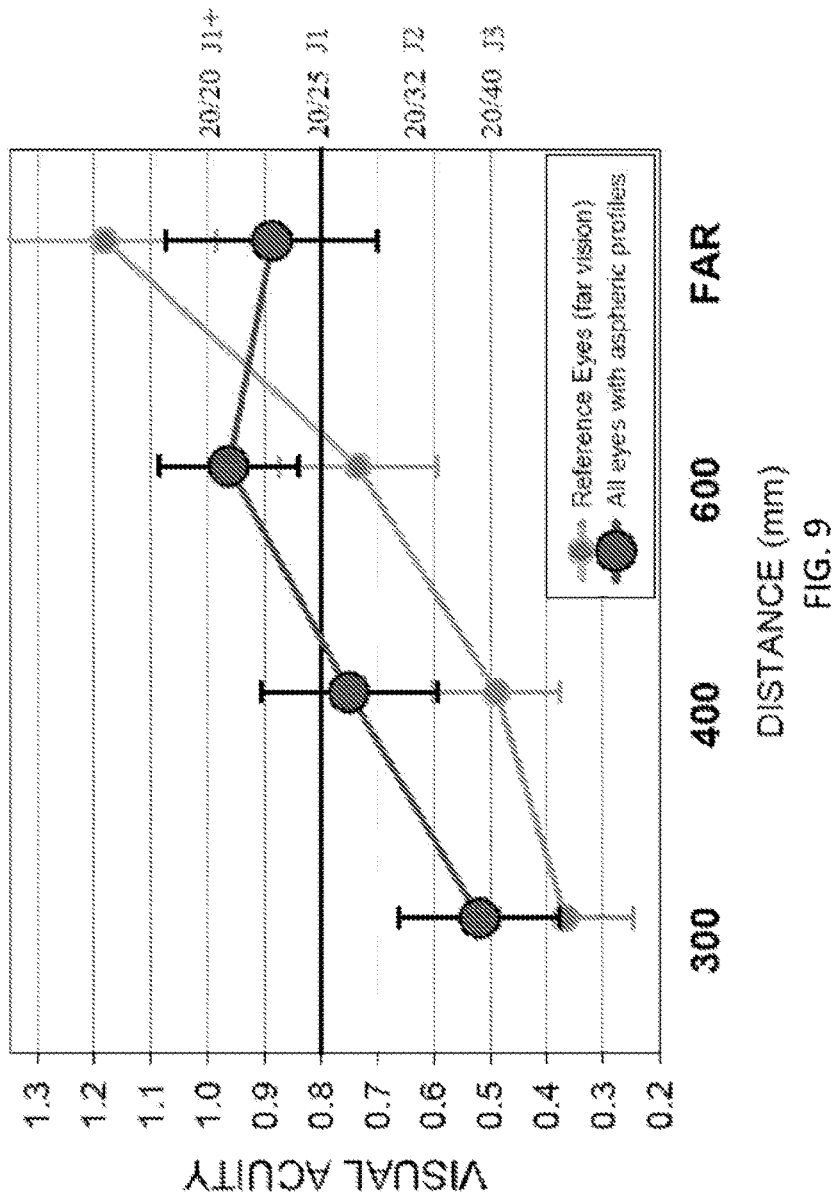
FIG. 9 shows the monocular visual acuity data for eyes receiving an initial refractive adjustment followed by an aspheric treatment (n=32) versus those eyes treated only for distance emmetropia (n=12).

To test the ability of the aspheric adjustment profiles to induce enough asphericity to provide patients with increased depth of focus, a series of subjects were implanted with the light adjustable lens after routine cataract surgery, given a prior treatment to correct for postoperative residual sphere and cylinder, and then given an aspheric adjustment using the corneal compensated versions of the profiles described in Example 1. FIG. 9 and Table 2 summarize the monocular visual acuity data for a series of 32 eyes adjusted with aspheric profiles possessing a beta value between 0.40 and 0.57. For comparison, the average uncorrected visual acuity values for 12 eyes implanted with a LAL and adjusted for distance emmetropia only, are displayed as well. All of the LALs received some type of primary adjustment before the application of the aspheric profile.

Inspection of the graph in FIG. 9 indicates several important features. The first is that, on average, from 40 cm to distance emmetropia, the patients adjusted with an aspheric treatment profile possessed uncorrected visual acuities between 20/20 and 20/32. In fact, as summarized in Table 2, 75% of the eyes treated with the aspheric profile treatment regimen, possess an uncorrected visual acuity of 20/32 or better from 40 cm to distance emmetropia. In contrast, inspection of the results for those eyes receiving treatment to correct for residual, spherical and spherocylindrical refractive errors, only, show that while the distance, uncorrected visual acuity results are better than the aspheric cases (83%>20/20 and 100%>20/25 or better), these eyes, as expected, have essentially no near vision capability, i.e. 8% (1/12) see at least 20/32 at 40 cm. Therefore, this data indicates that the application of the aspheric profiles to implanted LALs has the ability to increase the depth of focus of a patients' eye.

TABLE 1

Monocular visual acuity (VA) results for those eyes receiving an aspheric treatment (n = 32).

| VA | FAR | 60 cm | 40 cm | Far BCVA |
|---|---|---|---|---|
| ≥20/20 | 9/32 (28%) | 17/32 (53%) | 2/32 (6%) | 21/32 (65%) |
| ≥20/25 | 23/32 (72%) | 27/32 (84%) | 11/32 (35%) | 31/32 (97%) |
| ≥20/32 | 28/32 (88%) | 32/32 (100%) | 24/32 (75%) | 32/32 (100%) |
| ≥20/40 | 32/32 (100%) | 32/32 (100%) | 31/32 (97%) | 32/32 (100%) |
| ≥20/60 | 32/32 (100%) | 32/32 (100%) | 32/32 (100%) | 32/32 (100%) |

TABLE 2

Monocular visual acuity (VA) results for those LAL eyes adjusted for distance visual acuity only (n = 12).

| VA | FAR | 60 cm | 40 cm | Far BCVA |
|---|---|---|---|---|
| ≥20/20 | 10/12 (83%) | 1/12 (8%) | 0/12 (0%) | 12/12 (100%) |
| ≥20/25 | 12/12 (100%) | 3/12 (25%) | 0/12 (0%) | 12/12 (100%) |
| ≥20/32 | 12/12 (100%) | 8/12 (67%) | 1/12 (8%) | 12/12 (100%) |
| ≥20/40 | 12/12 (100%) | 12/12 (100%) | 7/12 (58%) | 12/12 (100%) |
| ≥20/60 | 12/12 (100%) | 12/12 (100%) | 12/12 (100%) | 12/12 (100%) |

Figure 10:
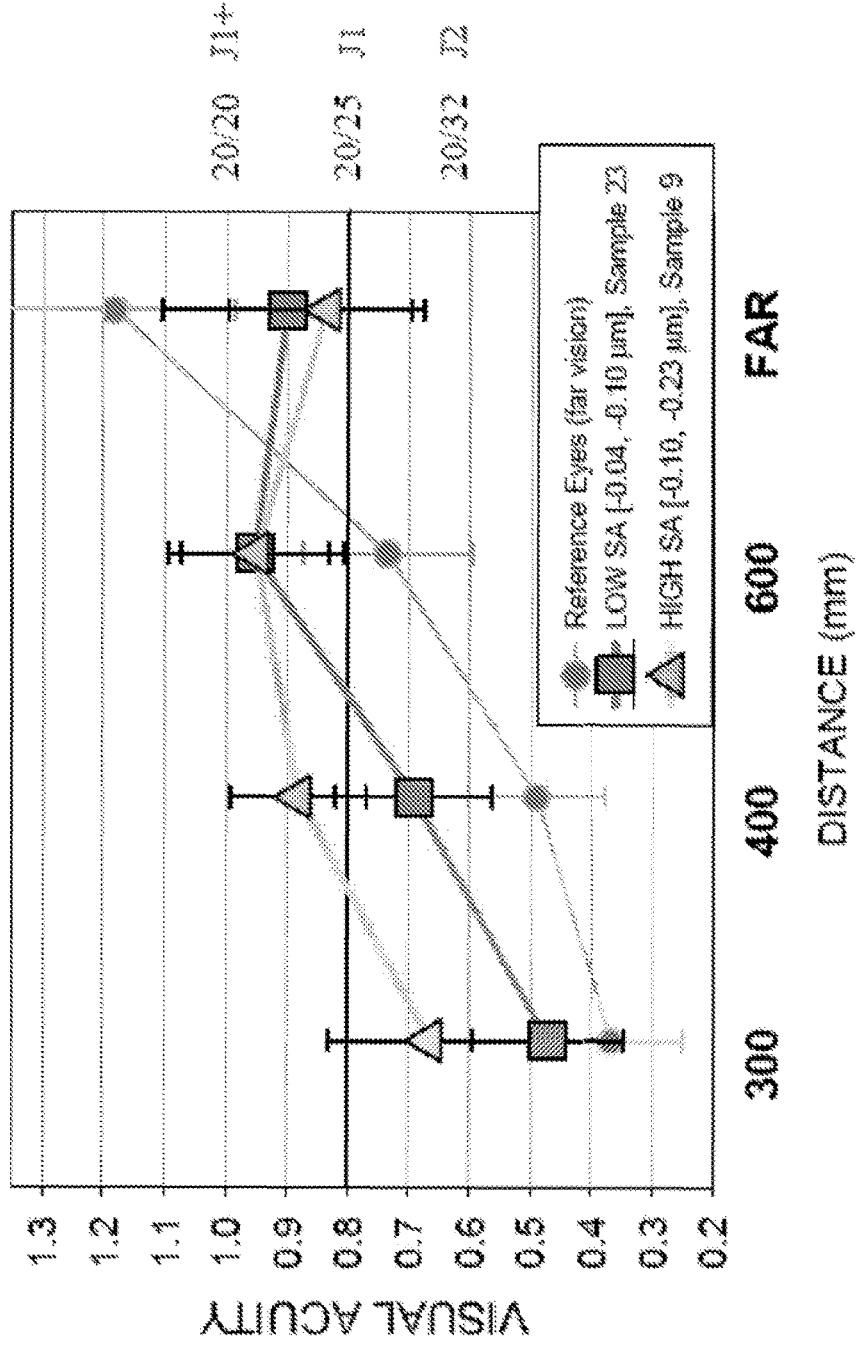
FIG. 10 shows the segregation of the monocular visual acuity data into high (n=9) and low (n=23) induced spherical aberration values. For comparison, those eyes (n=12) adjusted for distance emmetropia are also shown.

As indicated in FIG. 9, the total measured $4^{th}$ order spherical aberration over a 4 mm pupil in fee 32 eyes ranged from −0.04 µm to −0.23 µm. As stated above, theoretical considerations indicate that the ideal amount of final $4^{th}$ order spherical, aberration to provide optimal visual acuity between 40 cm and distance emmetropia is −0.125 µm. To consider the impact of this range of induced negative asphericity on the final visual acuities at different object distances, FIG. 10 segregates the 32 eyes into two groups: High Spherical Aberration (−0.10 μm to −0.23 μm) and Low Spherical Aberration (−0.04 μm to −0.10 μm). As expected, those eyes with higher amounts of induced negative spherical aberration, on average, show better visual acuities at 40 cm (78% 7/9 patients ≥20/25 or J1) then those with lower spherical aberration (22%, 5/23 patients ≥20/25 or J1) with a slight decrease in their distance visual acuities (56% vs 78% at 20/25). However, inspection of the VA acuity curves from 40 cm to distance emmetropia in FIG. 10, indicate that, on average, the curve is quite flat and the majority of the eyes possess visual acuities of 20/25 or better. Comparison again with the 12 eyes adjusted for distance emmetropia only, indicates that from 40 cm to distance emmetropia, the eyes that received some type of aspheric induction achieve much greater range of vision, i.e. increased depth of focus.

Figure 11:
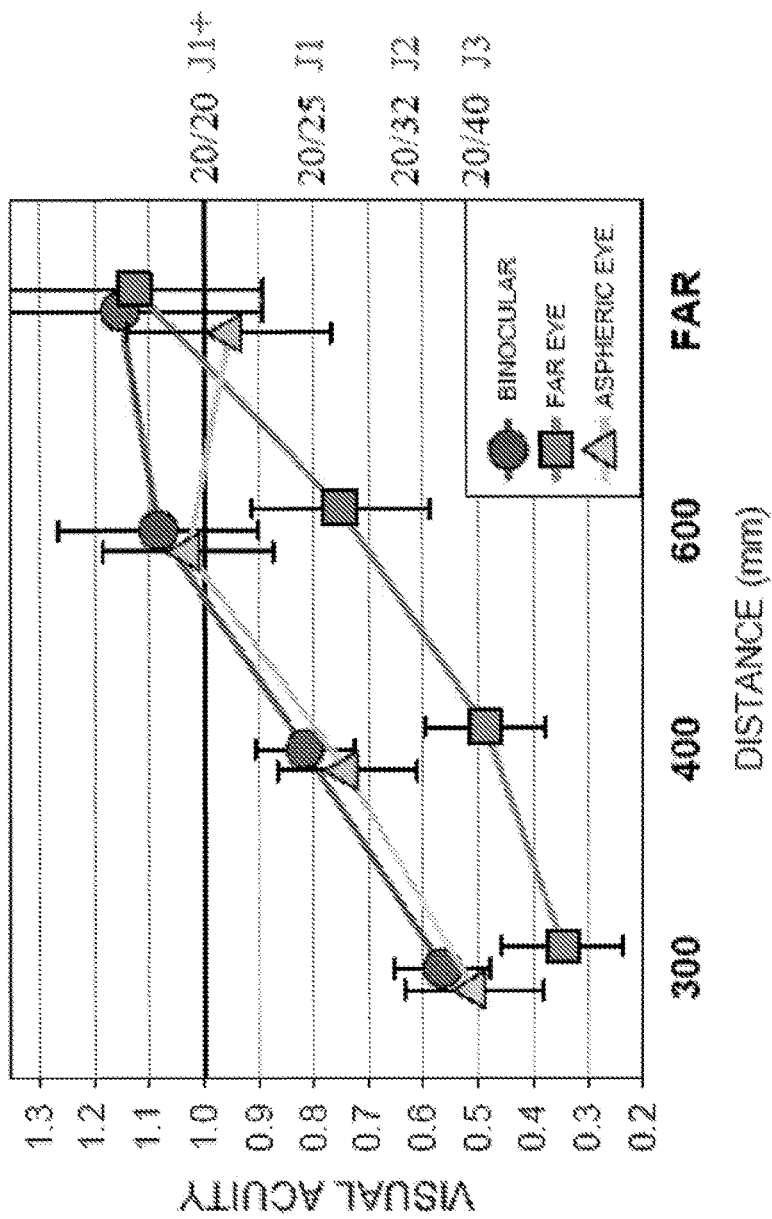
FIG. 11 shows a comparison of the monocular and the binocular visual acuities for a series of patients that were corrected for distance emmetropia in one eye and received an aspheric treatment in their fellow eye. The amount of induced asphericity ranged from −0.04 μm to −0.10 μm, referenced to a 4 mm pupil.
Figure 12:
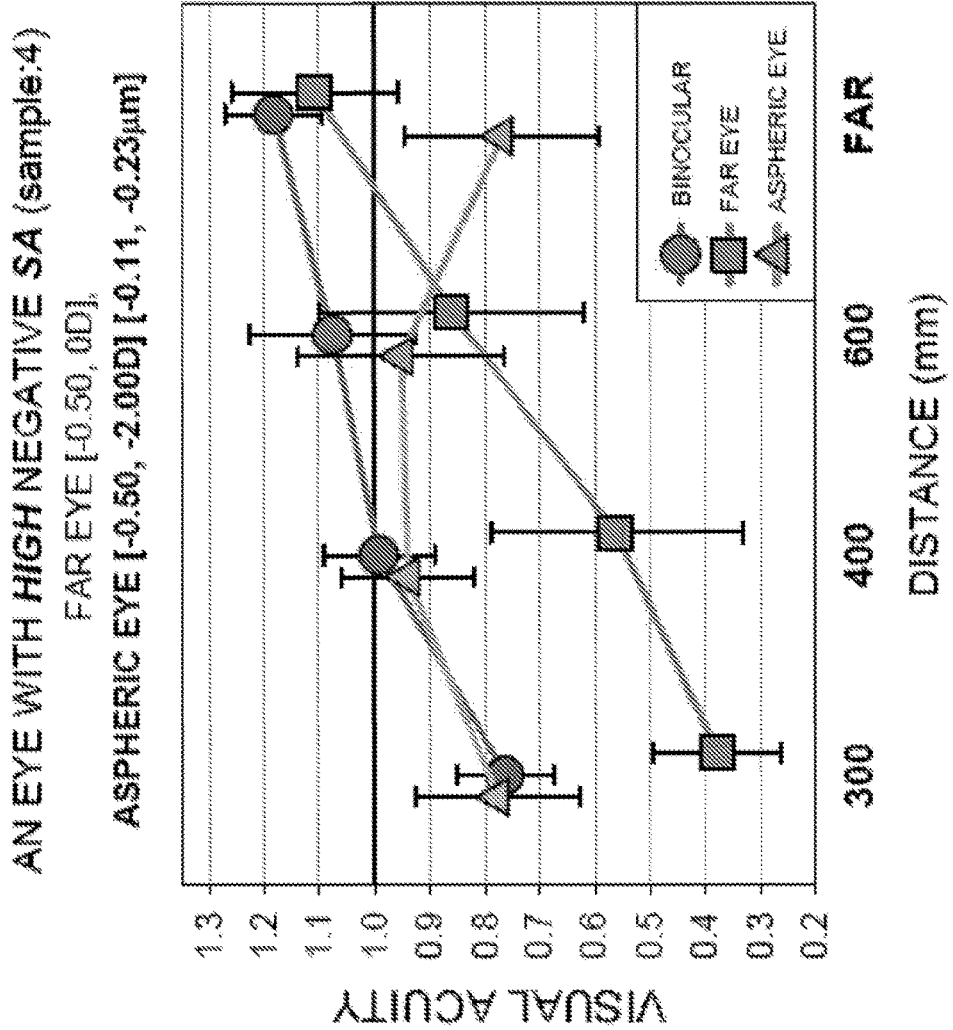
FIG. 12 shows a comparison of the monocular and binocular visual acuities for a series of patients that were corrected for distance emmetropia in one eye and received an aspheric treatment in their fellow eye. The amount of induced asphericity ranged from −0.11 μm to −0.23 μm, referenced to a 4 mm pupil.

The above discussion considered the monocular visual acuities of the treated eyes, only. However, one approach that will optimize post LAL implantation patients' vision at all distances is to correct one of the patients' eyes (usually the dominant eye) to distance emmetropia and then to adjust the other eye of the patient first to distance emmetropia followed by application of the aspheric treatment As an example of this procedure, consider the data displayed in FIG. 11 and Table 6, which displays both the monocular and binocular visual acuities for a series of patients (n=10) that had a low (−0.04 μm to −0.10 μm) amount of spherical aberration induced in one eye and the other eye was implanted with a LAL and adjusted for distance emmetropia. For the distance dominant eye, the final refraction varied between plano and −0.50 D. Inspection of the monocular visual acuity results for the two eyes displays the same visual characteristics already discussed; namely, the eye corrected for distance emmetropia displays excellent distance visual acuity, but rather poor near vision and the aspheric eyes display improved depth of focus at the expense of some distance visual acuity. However, the binocular visual acuity data indicates that combining the two eyes provide outstanding visual acuities from 40 cm to distance emmetropia. In fact, 100% of the patients possessed a visual acuity of 20/25 or better from 40 cm to distance emmetropia.

TABLE 3

Monocular visual acuity (VA) results for those eyes with low amounts of final $4^{th}$ order spherical aberration, −0.04 to −0.10 μm (n = 23).

| VA | FAR | 60 cm | 40 cm | Far BCVA |
|---|---|---|---|---|
| ≥20/20 (J1+) | 7/23 (30%) | 12/23 (8%) | 0/23 (0%) | 15/23 (65%) |
| ≥20/25 (J1) | 15/23 (74%) | 19/23 (83%) | 5/23 (22%) | 22/23 (96%) |
| ≥20/32 (J2) | 20/23 (100%) | 23/23 (100%) | 15/23 (65%) | 12/12 (100%) |
| ≥20/40 (J3) | 23/23 (100%) | 23/23 (100%) | 23/23 (100%) | 12/12 (100%) |
| ≥20/60 | 23/23 (100%) | 23/23 (100%) | 23/23 (100%) | 12/12 (100%) |

TABLE 4

Monocular visual acuity (VA) results for those eyes with high amounts of final 4th order spherical aberration, −0.11 to −0.23 μm (n = 9).

| VA | FAR | 60 cm | 40 cm | Far BCVA |
|---|---|---|---|---|
| ≥20/20 (J1+) | 2/9 (22%) | 4/9 (8%) | 2/9 (22%) | 6/9 (67%) |
| ≥20/25 (J1) | 5/9 (56%) | 7/9 (78%) | 7/9 (78%) | 8/9 (89%) |
| ≥20/32 (J2) | 8/9 (89%) | 8/9 (89%) | 9/9 (100%) | 9/9 (100%) |
| ≥20/40 (J3) | 9/9 (100%) | 9/9 (100%) | 9/9 (100%) | 9/9 (100%) |
| ≥20/60 | 9/9 (100%) | 9/9 (100%) | 9/9 (100%) | 9/9 (100%) |

TABLE 5

Binocular visual acuity (VA) results for those eyes with low amounts of final 4th order spherical aberration, −0.04 to −0.10 mm in their non-dominant eye and with their other eye adjusted for distance emmetropia. The refraction in the dominant eye ranged from +0.25 D to −0.25 D (n = 10).

| VA | FAR | 60 cm | 40 cm | 30 cm |
|---|---|---|---|---|
| ≥20/20 (J1+) | 6/10 (60%) | 8/10 (80%) | 1/10 (10%) | 0/10 (0%) |
| ≥20/25 (J1) | 10/10 (100%) | 10/10 (100%) | 4/10 (40%) | 0/10 (0%) |
| ≥20/32 (J2) | 10/10 (100%) | 10/10 (100%) | 10/10 (100%) | 3/10 (30%) |
| ≥20/40 (J3) | 10/10 (100%) | 10/10 (100%) | 10/10 (100%) | 8/10 (80%) |
| ≥20/60 | 10/10 (100%) | 10/10 (100%) | 10/10 (100%) | 10/10 (100%) |

Combining this binocular approach with those eyes having high amounts of induced asphericity (−0.11 μm to −0.23 μm), indicates that 100% (4/4) of the patients possessed an uncorrected visual of 20/25 or better from 40 cm to distance emmetropia.

TABLE 6

Binocular visual acuity (VA) results for those eyes with high amounts of final 4th order spherical aberration, −0.11 to −0.23 μm in their non-dominant eye and with their other eye adjusted for distance emmetropia. The refraction in the dominant eye ranged from +0.25 D to −0.25 D (n = 4).

| VA | FAR | 60 cm | 40 cm | 30 cm |
|---|---|---|---|---|
| ≥20/20 (J1+) | 4/4 (100%) | 3/4 (75%) | 1/10 (10%) | 0/4 (0%) |
| ≥20/25 (J1) | 4/4 (100%) | 4/4 (100%) | 4/4 (100%) | 1/4 (25%) |
| ≥20/32 (J2) | 4/4 (100%) | 4/4 (100%) | 4/4 (100%) | 4/4 (100%) |
| ≥20/40 (J3) | 4/4 (100%) | 4/4 (100%) | 4/4 (100%) | 4/4 (100%) |
| ≥20/60 | 4/4 (100%) | 4/4 (100%) | 4/4 (100%) | 4/4 (100%) |

Example 3

General examples disclosed herein include an optical element composed of matrix polymer and a modulating composition (MC) that can be polymerized by an external stimulus (e.g. heat; light, etc) to control the amount of induced asphericity.

In each of the aforementioned examples, the lens may include an optical element that is a lens. In additional examples, the optical element is an intraocular lens (IOL). Also, the amount of induced asphericity is controlled by the application of a specific spatial irradiance profile. In some examples, the amount of induced asphericity is induced monocularly to induce extended depth of focus.

In particular examples, the amount of induced asphericity is tailored to provide intermediate vision (60-80 cm) or near vision (30-40 cm). In specific embodiments, the amount of induced asphericity can be customized for specific individual values.

In certain embodiments, the amount of induced, asphericity is induced binocularly to induce extended depth of focus. In particular examples, one eye is tailored for intermediate (60-80 cm) vision by the induction of a particular value of asphericity and the other eye is corrected for distance emmetropia. In alternate embodiments, one eye is tailored for near vision (30-40 cm) by the induction of a particular value of asphericity and the other eye is corrected for distance emmetropia. In further embodiments, both eyes are tailored for intermediate (60-80 cm) vision by the induction of particular value of asphericity. In yet another embodiment, both eyes are tailored for near (30-40 cm) vision by the induction of particular value of asphericity. In some embodiments, one eye is tailored for intermediate (60-80 cm) vision by the induction of negative asphericity and the other eye is tailored for intermediate vision (60-80 cm) vision by the induction of positive asphericity. In particular embodiments, one eye is tailored for near vision (30-40 cm) vision by the induction of negative asphericity and the other eye is tailored for near vision (30-40 cm) vision by the induction of positive asphericity.

In some examples, the amount of induced asphericity of the lens is tailored to compensate for the spherical aberration of the cornea. In other examples, the amount of induced asphericity of both lenses are tailored to compensate for the spherical aberration of their respective corneas. In alternate examples, one lens is adjusted to remove the spherical aberration of the entire eye and the other lens is adjusted to induce asphercity for intermediate vision (60-80 cm). In some examples, one lens is adjusted to remove the spherical aberration, of the entire eye and the other lens is adjusted to induce asphercity for near vision (30-40 cm).

REFERENCES

All patents and publications mentioned in the specification are indicative of the level of those skilled in the art to which the invention pertains. All patents and publications are herein incorporated by reference in their entirety to the same extent as if each individual publication was specifically and individually indicated to be incorporated by reference.

Patents
U.S. Pat. No. 4,260,725
U.S. Pat. No. 5,225,858
U.S. Pat. No. 5,236,970
U.S. Pat. No. 5,278,258
U.S. Pat. No. 5,376,694
U.S. Pat. No. 5,444,106
PUBLICATIONS
Camellin. M, Calossi A. A new formula for intraocular lens power calculation after refractive corneal surgery. J Refract Surg. 2006; 22(2): 187-99.

Chokshi A R, Latkany R A, speaker MG Yu G. Intraocular lens calculations after hyperopic refractive surgery. Ophthalmology 2007; 104(11): 2044-9.

Ciuffreda; Accommodation, the Pupil, and Presbyopia, Chapter 4 in Borisch's Clinical Refraction pp. 77-120, W.B. Saunders Company (1998).

E. J. Fernández, S. Manzanera, P. Piers, P. Artal; Adaptive Optics Visual Simulator", J. Refract. Surg., 2002; 18: S634-S638.

Ellingson, F. T.; Explanation of 3M Diffractive Intraocular Lenses, J, Cataract and Refractive Surgery, 1990; 1.6: 697-701.

Fam H B, Lim K L. A comparative analysis of intraocular lens power calculation methods after myopic excimer laser surgery. J Refract Surg. 2008; 24:355-360.

Feiz V, Moshirfar M, Mannis M J, Reilly C D, Garcia-Ferrer F. Caspar J J, Lim M C. Nomogram-based intraocular lens power adjustment after myopic photorefractive keratectomy and LASIK, Ophthalmology 2005; 112:1381-1387.

Hansen, T. E., Corydon, L., Krag, S., and Thim, K., New Multifocal Intraocular Lens Design, J, Cataract and Refractive Surgery, 1990; 16:38-41.

Helmholtz, H., Treatise on Physiological Optics (translated by Sohthall JPC), New York: Dover. (1969).

Jin G C, Crandall A S, Jones J J. Intraocular lens exchange due to incorrect lens power. Ophthalmology. 2007; 114:417-424.

Latkany R A, Chokshi A R, Speaker M G, Abramson J, Soloway B D, Yu G. Intraocular lens calculations after refractive surgery. J Cataract Refract Surg. 2005; 31:562-570.

Mackool R J Ko W, Mackool R. Intraocular lens power calculation after laser in situ keratomileusis: aphakic refraction technique. J Cataract Refract Surg. 2006; 32:435-437.

Mamalis N, Brubaker J. David J, Espandar L, Werner L. Complications of foldable intraocular lenses requiring explanation or secondary intervention—2007 survey update. J Cataract Refract Surg. 2008; 34:1584-1591.

Murphy C, Tuft S J, Minassian D C. Refractive error and visual outcome after cataract extraction. J Cataract Refract Surg. 2002;28(1):62-66.

Narvaez J, Zimmerman G, Stulting R D, Chang D H. Accuracy of intraocular lens power prediction using the Hoffer Q, Holladay 1, Holladay 2, and SRK/T formulas, J Cataract Refract Surg. 2006; 32:2050-2053.

Olsen T. Sources of error in intraocular-lens power calculation. J Cataract Refract Surg. 1992; 18:125-129.

Packer M. Brown L K, Hoffman R S, Fine I H. Intraocular lens power calculation after incisional and thermal keratorefractive surgery. J Cataract Retract Surg. 2004; 30:1430-1434.

Packer, M.; Fine, I H.; Hoffman, R. S., Refractive Lens Exchange with the Array Multifocal Intraocular Lens, H., J. Cataract and Refract Surgery, 2002; 28:421-424.

Preussner P R., Wahl J, Weitzel D, Berthold S, Kriechbaum K, Findl O. Predicting postoperative intraocular lens position and refraction. J. Cataract Refract Surg, 2004; 30:2077-2083.

Steiner, R. F., Aler, B. L., Trentacost, D. J., Smith, P. J., Taratino, N. A., A Prospective Comparative Study of the AMO Array zonal-progressive multifocal silicone intraocular lens and a monofocal intraocular lens, Opthalmology, 1999; 106(7): 1243-1255.

Sun, X. Y.; Vicary, D.; Montgomery, P.; Griffiths, M. Toric intraocular lenses for correcting astigmatism in 130 eyes. Ophthalmology, 2000; 107(9), 1776-81.

Thibos, L. N.; Hong, X.; Bradley, A.; Applegate, R. A, Accuracy and Precision of Objective Refraction from Wavefront Aberrations, Journal of Vision, 2004; 4: 329-351.

Wang L, Booth M A, Koch D D. Comparison of intraocular lens power calculation methods in eyes that have undergone LASIK. Ophthalmology 2004; 111:1825-1831.

Although the present invention and its advantages have been described in detail, it should be understood that various changes, substitutions and alterations can be made herein without departing from the spirit and scope of the invention as defined by the appended claims. Moreover, the scope of the present application is not intended to be limited, to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture compositions of matter, means, methods, or steps.

What is claimed is:

1. A method of forming an aspheric lens for presbyopia reduction by changing its shape, the method comprising:
providing a light-adjustable lens for a presbyopic eye with
   a positive ocular asphericity, the lens including
   a first polymer matrix; and
   a modifying composition,
      dispersed in the first polymer matrix, and
      capable of photoinduced polymerization; and
irradiating the lens with a spatially defined irradiance profile described by $$\text{Profile}(\rho)=\text{SCN}(\rho)+\beta\text{Asph}(\rho);$$

wherein
   $\rho$ is a normalized radial coordinate, $\beta$ is a weighting factor sufficiently large to induce a negative asphericity in the lens large enough to overcompensate the positive ocular asphericity into a negative ocular asphericity, thereby reducing the presbyopia of the eye:
   $\text{SCN}(\rho)$ is one of a spherical, a spherocylindrical and a power neutral spatial irradiance profile; and
   $\text{Asph}(\rho)=A\rho^4-B\rho^2+1$ is an asphericity-inducing irradiance profile,
in order to photoinduce polymerization in the modifying composition and thereby changing the shape of the lens into an aspheric lens having the negative asphericity and thereby an extended depth of focus.

2. The method of claim 1, wherein:
$A=B=4$.

3. The method of claim 1, wherein
$\beta$ is in a range from 0 to 1.

4. The method of claim 3, wherein:
$\beta$ is in a range from 0.05 to 0.57.

5. The method of claim 4, wherein:
$\beta$ is in a range from 0.30 to 0.57.

6. The method of claim 1, comprising:
irradiating the aspheric lens with a second irradiation procedure to photoinduce polymerization in a remaining unpolymerized portion of the modifying composition.

7. The method of claim 1, the irradiating comprising:
irradiating the lens with a spatially defined irradiance profile so that after the irradiation a wavefront of the aspheric lens has a $4^{th}$ order spherical aberration at a 4 mm measurement aperture in a range from $-0.006$ μm to $-0.285$ μm.

8. The method of claim 1, the irradiating comprising:
irradiating the lens with a spatially defined irradiance profile so that after the irradiation a wavefront of the aspheric lens has a $4^{th}$ order spherical aberration at a 4 mm measurement aperture in a range from $-0.04$ μm to $-0.010$ μm.

9. The method of claim 1, the irradiating comprising:
irradiating the lens with a spatially defined irradiance profile so that after the irradiation a wavefront of the aspheric lens has a $4^{th}$ order spherical aberration at a 4 mm measurement aperture in a range from $—0.010$ μm to $—0.23$ μm.

10. The method of claim 1, wherein:
the $4^{th}$ order spherical aberration is a $Z(12)$ type aberration.

11. The method of claim 1, the irradiating comprising:
irradiating the lens with a spatially defined irradiance profile so that after the irradiation a wavefront of the aspheric lens has a magnitude of a $6^{th}$ order aberration at a 4 mm measurement aperture is smaller than 0.04 μm.

12. The method of claim 11, the irradiating comprising:
irradiating the lens with a spatially defined irradiance profile so that after the irradiation a wavefront of the aspheric lens has a magnitude of a $6^{th}$ order aberration at a 4 mm measurement aperture is smaller than 0.01 µm.

13. The method of claim 1, the providing comprising:
providing a modifying compound that includes one of a monomer and a macromer, with an endcapping that includes a photopolymerizable group to facilitate the photoinduced polymerization.

14. The method of claim 1, the providing comprising:
providing a modifying compound that includes a photoinitiator to initiate a photoinduced polymerization of the photopolymerizable group.

15. The method of claim 14, the irradiating comprising:
irradiating the lens in order to photoinduce the polymerization of the modifying composition into a second polymer matrix.

\* \* \* \* \*